(12) United States Patent
Khan et al.

(10) Patent No.: US 12,152,046 B2
(45) Date of Patent: Nov. 26, 2024

(54) OLEIC ACID DERIVATIVES, PHARMACEUTICAL COMPOSITION OR FOOD COMPOSITION COMPRISING SAID OLEIC ACID DERIVATIVES, AND THEIR USES

(71) Applicants: UNIVERSITÉ DE BOURGOGNE, Dijon (FR); INSERM (INSTITUT NATIONAL DE LA SANTÉ ET DE LA RECHERCHE MÉDICALE), Paris (FR)

(72) Inventors: Naim Khan, Quetigny (FR); Sylvain Juge, Dijon (FR); Aziz Hichami, Is Sur Tille (FR); Jérôme Bayardon, Dijon (FR); Floriane Mangin, Allain (FR); Amira Khan, Quetigny (FR)

(73) Assignees: UNIVERSITÉ DE BOUROGNE, Dijon (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 437 days.

(21) Appl. No.: 17/059,382

(22) PCT Filed: May 27, 2019

(86) PCT No.: PCT/EP2019/063670
§ 371 (c)(1),
(2) Date: Nov. 27, 2020

(87) PCT Pub. No.: WO2019/228994
PCT Pub. Date: Dec. 5, 2019

(65) Prior Publication Data
US 2021/0238209 A1   Aug. 5, 2021

(30) Foreign Application Priority Data
May 28, 2018   (EP) .................................... 18305647

(51) Int. Cl.
| | | |
|---|---|---|
| *C07F 9/40* | (2006.01) | |
| *A23L 29/00* | (2016.01) | |
| *A23L 33/00* | (2016.01) | |
| *A61P 3/04* | (2006.01) | |
| *C07D 305/06* | (2006.01) | |

(52) U.S. Cl.
CPC .......... *C07F 9/4015* (2013.01); *A23L 29/035* (2016.08); *A23L 29/045* (2016.08); *A23L 29/05* (2016.08); *A23L 33/30* (2016.08); *A61P 3/04* (2018.01); *C07D 305/06* (2013.01)

(58) Field of Classification Search
CPC .............................. C07F 9/4015; C07D 305/06
See application file for complete search history.

(56) References Cited

U.S. PATENT DOCUMENTS

| | | | | |
|---|---|---|---|---|
| 2006/0122246 A1 | 6/2006 | Msika et al. | | |
| 2013/0183255 A1* | 7/2013 | Saunois | .................. | A61P 17/00 424/59 |

FOREIGN PATENT DOCUMENTS

| | | | | |
|---|---|---|---|---|
| WO | 96/18600 | 6/1996 | | |
| WO | 02/00042 | 1/2002 | | |
| WO | WO-0200042 A2 * | 1/2002 | ............. | A23D 7/011 |
| WO | 2013/121449 | 8/2013 | | |
| WO | 2013/149025 | 10/2013 | | |
| WO | WO-2014056939 A1 * | 4/2014 | ........... | A61K 9/0002 |
| WO | 2018/132876 | 7/2018 | | |

OTHER PUBLICATIONS

Nishizawa et al. Tetrahedron Letters 1983, 24, 4447-4450 (Year: 1983).*
CAS Registry No. 150-81-2, which entered STN on Nov. 16, 1984 (Year: 1984).*
Bisogno et al. Biochimica et Biophysica Acta 2006, 1761, 205-212 (Year: 2006).*
International Search Report for PCT/EP2019/063670 mailed Aug. 6, 2019, 7 pages.
Written Opinion of the ISA for PCT/EP2019/063670 mailed Aug. 6, 2019, 8 pages.
Quistad et al., "Fatty Acid Amide Hydrolase Inhibition by Neurotoxic Organophosphorus Pesticides", Toxicology and Applied Pharmacology, May 1, 2001, vol. 173, No. 1, pp. 48-55.
Bisogno et al., "Development of the first potent and specific inhibitors of endocannabinoid biosynthesis", Biochimica et Biophysica Acta (BBA), Feb. 1, 2006, vol. 1761, No. 2, pp. 205-212.
Cisneros et al., "Structure-Activity Relationship of a Series of Inhibitors of Monoacylglycerol Hydrolysis-Comparison with Effects upon Fatty Acid Amide Hydrolase", Journal of Medical Chemistry, Oct. 1, 2007, vol. 50, No. 20, pp. 5012-5023.
Marrs et al., "Dual Inhibition of α/β-Hydrolase Domain 6 and Fatty Acid Amide Hydrolase Increases Endocannabinoid Levels in Neurons", The Journal of Biological Chemistry, Aug. 19, 2011, vol. 286, No. 33, pp. 28723-28728.
Oberland et al., "CD36 is involved in oleic acid detection by the murine olfactory syster", Frontiers in Cellular Neuroscience, Sep. 16, 2015, vol. 9, No. 366, 18 pages.
Ulven et al., "Dietary Fatty Acids and Their Potential for Controlling Metabolic Diseases Through Activation of FFA4/GPR120", Annual Review of Nutrition, Jul. 17, 2015, vol. 35, No. 1, pp. 239-263.

(Continued)

*Primary Examiner* — Matthew P Coughlin
(74) *Attorney, Agent, or Firm* — NIXON & VANDERHYE

(57) ABSTRACT

Disclosed is an oleic acid derivative including a hydrophobic part C17H33 linked to a particular polar head part "A", especially for use as a medicament, for instance, for the treatment of a disorder caused by the GPR120 receptor and/or the CD36 receptor, including administering to a subject in need thereof a therapeutically effective amount of the oleic acid derivative or of the pharmaceutical composition. Also disclosed is the use of the oleic acid derivative as a food composition.

19 Claims, 6 Drawing Sheets

(56) References Cited

OTHER PUBLICATIONS

Ozdener et al., "CD36-and GPR120-mediated Ca2+ Signaling in Human Taste Bud Cells Mediates Differential Reponses to Fatty Acids and is Altered in Obese Mice", Gastroenterology, Apr. 1, 2014, vol. 146, No. 4, 19 pages.

Kuda et al., "Sulfo-N-succinimidyl Oleate (SSO) Inhibits Fatty Acid Uptake and Signaling for Intracellular Calcium via Binding CD36 Lysine 164: SSO Also Inhibits Oxidized Low Density Lipoprotein Uptake by Macrophages", the Journal of Biological Chemistry, May 31, 2013, vol. 288, No. 22, pp. 15547-15555.

Godinot et al., Activation of Tongue-Expressed GPR40 and GPR120 by Non Caloric Agonists is Not Sufficient to Drive Preference in Mice, Neuroscience, Oct. 2013, vol. 250, pp. 20-30.

\* cited by examiner

OLEIC ACID DERIVATIVES, PHARMACEUTICAL COMPOSITION OR FOOD COMPOSITION COMPRISING SAID OLEIC ACID DERIVATIVES, AND THEIR USES

This application is the U.S. national phase of International Application No. PCT/EP2019/063670 filed May 27, 2019 which designated the U.S. and claims priority to EP patent application Ser. No. 18305647.2 filed May 28, 2018, the entire contents of each of which are hereby incorporated by reference.

FIELD OF THE INVENTION

The present invention relates to field of products dedicated to the therapeutic treatment or cosmetic treatment of weight-related disorders such as excess weight or obesity, linked to excessive intake of dietary fatty acids.

Especially, the present invention refers to compounds that are able to bind to or to modulate the activity of lingual taste receptors, such as CD36 and/or GPR120 that are involved in the detection and orosensory perception of these fatty acids. In particular, the compounds of the invention are derived from a natural fatty acid, which is oleic fatty acid.

The present invention also refers to the use of these compounds for the cosmetic or the therapeutic treatment linked to weight-related disorders.

DESCRIPTION OF RELATED ART

Defined as a medical condition in which excess body fat has accumulated to the extent that it may have a negative impact on health, obesity is one of the main priorities of the World Health Organization (WHO report No. 311, 2016, www.who.int/mediacentre/factsheets/fs311/en/), as regards disease prevalence and management. Indeed, on a world scale, 600 million people are obese, thus representing about 15 to 30% of the population in industrialized countries. It is also estimated that 43 million kids under the age of five are overweight and thus have a higher risk of developing obesity once they become adult. Moreover, the increasing prevalence of obesity in the global population goes along with an increased proportion of excess weight mothers or obese women at the start of their pregnancies. Yet, obese mothers are much more likely to give birth to obese children (called macrosomic children), especially if they suffer from gestational diabetes or from metabolic syndrome in pregnancy. In France, excess weight and obesity together affect more than 46% of adults and 19% of children (OBEpi 2012 Report, http://www.roche.fr/content/dam/roche_france/fr_FR/doc/obepi_2012.pdf).

In general, the main risk factor which especially contributes to increase the energy balance and to produce excess weight or even obesity or to increase the fat mass is a high-energy density diet delivering a low satiety feeling, resulting from a high proportion of energy originating from fats (vegetable oils and animal fats) (i.e., hyperlipidic diet). This high-energy density diet has become a part of our way of life and eating behavior which have been fundamentally changed in the $20^{th}$ century.

At present, dietary fat intake is almost 40% of the population in Western countries. This excessive consumption of lipids favors the incidence of plethora diseases, such as obesity mentioned above, but also type 2 diabetes, etc., with important medico-economic consequences.

Adapted dietetic and hygienic measures, combining a balanced diet and a regular physical activity, do represent the simplest way to fight against excess fat ingestion or excess weight. Yet practicing a regular physical activity is constraining and, moreover, the benefits of a restrictive diet are often limited by a weight rebound effect when starting normal eating and drinking again.

Therefore, it is important to develop compounds to prevent and treat weight disorders.

During the course of last couple of years, several strategies have been developed by industries/scientists to decrease fat contents in the diet.

Two main classes of compounds/solutions, namely "fat substitutes" or "fat mimetics" have been developed to achieve this goal. These "fat substitutes" or "fat mimetics" contain saturated fat and protein- or carbohydrate-derived substances. However, these compounds are lesser palatable than natural fat and they are not, strikingly, devoid of calories, though they bring lesser calories than natural fat.

The recent discovery of fat taste as the sixth taste modality opens the door for the synthesis of a new class of molecules as taste modulators. Indeed, the sense of taste plays a key role in guiding the decision to ingest calorie rich nutritive food.

In fact, during food intake, the sapid molecules, dissolved in the saliva, activate lingual taste receptors situated at the apical pole of the taste bud cells, localized at the level of the papillae which are distributed in the lingual epithelium. A taste bud is a cluster of cells that comprises of a taste pore and four cell types with distinct functions. Type I cells (supporting cells) respond to salty substances, type II (receptor) cells respond to sweet, bitter and umami substances, type III (presynaptic) cells communicate via a synapse with the nerves, and the type IV cells (basal cells) are differentiated into types I, II and III cells. There are also progenitor cells, localized around taste buds, multiply and migrate inside the papilla. All the differentiated taste cells are subjected to a continuous renewal with a half-life of about 10 days.

The taste receptors (TR), present on the taste bud cells, are chemical motifs (homo- or heterodimeric), inserted into the plasma membrane of these lingual cells. T2R receptors would be involved in the perception of bitter or toxic flavors (Nelson G. et al. "Mammalian sweet taste receptors", *Cell.* 2001 Aug. 10, 106(3), 381-90). The T1R2/T1R3 heterodimer detects sweet flavors (Montmayeur J. P., Liberles S. D. et al. "candidate taste receptor gene near a sweet taste locus", Nat. Neurosci. 2001 May, 4(5), 492-8), while the T1R1/T1R3 heterodimer is sensitive to umami (Chaudhari N. et al., "A metabotropic glutamate receptor variant functions as a taste receptor", *Nat. Neurosci.* 2000 February, 3(2), 113-9).

The detection of dietary lipids along the oro-intestinal tract could take place through lipid-specific sensors. Lipid-specific binding proteins, expressed in the oral cavity and intestine, might perform this role. In accordance with this hypothesis, the recent data shows that the CD36 receptor, expressed on lingual papillae, plays a role in the oro-sensory perception of dietary lipids (El-Yassimi A. et al. "Linoleic acid induces calcium signaling, Src kinase phosphorylation, and neurotransmitter release in mouse CD36-positive gustatory cells", *J. Biol. Chem.* 2008 May 9, 283(19), 12949-59 and Dramane G. et al. "STIM1 regulates calcium signaling in taste bud cells and preference for fat in mice", *J. Clin. Invest.* 2012 June, 122(6), 2267-82).

In addition, GPR120, a member of the G-protein coupled receptors (GPCR) family, has been identified in taste bud cells in mouse and human beings (Ozdener M. H. et al. "CD36- and GPR120-mediated $Ca^{2+}$ signaling in human taste bud cells mediates differential responses to fatty acids and is altered in "obese mice", *Gastroenterology* 2014 April, 146(4), 995-1005; Dramane G. et al., "Cell signaling mechanisms of gustatory perception of lipids: can the taste cells be the target of anti-obesity agents", *Curr. Med. Chem.* 2011, 18(22), 3417-22).

Moreover, recent studies have clearly shown that CD36 and GPR120 act as lipid-taste receptors in mice and human (Gilbertson T. A., Khan N. A. "Cell signaling mechanisms of oro-gustatory detection of dietary fat: advances and challenges", *Prog. Lipid. Res.* 2014 January, 53, 82-92). These observations raise the possibility of a $6^{th}$ taste modality, devoted to the perception of the fat, present in our diet. Interestingly, the GPR40, a GPCR, was detected in mice, but not in human fungiform taste buds (Matsumura S. et al., "GPR expression in the rat taste bud relating to fatty acid sensing", *Biomed. Res.* 2007 February, 28, 49-55).

In addition, it has been observed that oro-sensory perception of dietary fat varies in individual, thus influencing nutritional status.

Indeed, it has been recently shown that there is a difference in the oro-sensory detection of fatty acids between lean and obese subjects. The threshold of gustatory perception of dietary lipids, such as oleic acid, is increased in obese subjects (Daoudi H. et al., "Oral Fat Sensing and CD36 Gene Polymorphism in Algerian Lean and Obese Teenagers", *Nutrients*. 2015 November 4, 7(11), 9096-9104). It has also been demonstrated that the genetic polymorphism of the CD36 gene correlates to a decrease in oro-sensory detection of dietary lipids in obese subjects (Mrizak I. et al., "The A allele of cluster of differentiation 36 (CD36) SNP 1761667 associates with decreased lipid taste perception in obese Tunisian women. *Br. J. Nutr.* 2015 April 28, 113(8), 1330-7). Consequently, the obese subjects have been considered as "hyposensitive" to detect dietary fatty acids and they will eat lipids in high quantity in order to regulate the "lipid-mediated" satiety. Similarly, obese mice, maintained on a high-fat diet, possess decreased lingual CD36 mRNA and protein levels. Hence, the decreased lingual CD36 expression in obese subjects would result in decreased signaling to brain and then to gut so as to control the satiety via the secretion of intestinal peptides/hormones. Therefore, the obese subjects eat more fat to trigger satiation.

Hence, several private companies and scientific groups have started to orient their R&D to elaborate a program on fat taste enhancers or fat taste agonists.

For instance, the publication of Godinot N. et al. ("Activation of tongue-expressed GPR40 and GPR120 by non-caloric agonists is not sufficient to drive preference in mice", *Neuroscience* 2013, 250, 20-30) describes six commercially available non-caloric agonists of GPR40 and two commercially available non-caloric agonists of GPR120 (compound 12 and compound 16, FIG. 1 of the same article). Godinot et al. assert the effects of these agonists as taste-triggering agents in mice.

However, they report that these agonists fail to initiate in mice a preference in the two-bottle preference tests with intralipid (control) and the agonists, i.e.: intralipid is highly preferred, whereas mice do not show any preference for the tested agonists.

Hence, there is a need to develop new non-caloric, but palatable, compounds that can mimic natural caloric fatty acids and can trigger "fat-like taste", thus contributing to less dietary fat intake.

Therefore, there is a need in the art for providing new non-caloric compounds that act as agonists of the fast taste receptors, such as GPR120 and/or CD36, that is to say which are able to exhibit a similar or the same affinity as natural dietary fatty acids and which are able to strongly bind to these taste receptors so as to trigger fat-like taste without any caloric value.

There is also a need in the art that these non-caloric compounds are able to activate the GPR120 and/or CD36 receptors in order to trigger fast taste, this taste leading preferably to preference for these non-caloric compounds. There is indeed a need to provide palatable non-caloric agonists/analogues of GPR120 and/or CD36 receptors.

There is also a need in the art for an easily feasible and reproducible method for obtaining such non-caloric compounds.

It is also useful to develop therapeutic treatments to prevent and treat weight disorders and diseases linked to weight disorders, i.e.: obesity, type 2 diabetes, etc., and to develop cosmetic strategies to allow people who are in good health to stabilize a weight as low as possible as long as these values do not have a pathological character and/or to stay slim.

SUMMARY OF THE INVENTION

The present invention meets these needs since the inventors surprisingly discovered that some oleic acid derivatives of formula (I) below are able to act as Fatty Acid Analogues (FAA), while being low-caloric and palatable.

Herein, FAA means a compound which acts as a natural dietary fatty acid, such as oleic acid (OA), but with little caloric content and having a gustatory preference as or more than lipids.

Especially, the inventors have discovered that the oleic acid derivatives of formula (I) are agonists of the oro-sensory fast-taste receptors CD36 and/or GPR120 which are involved in taste perception of dietary lipid. Hence, the oleic acid derivative plays a role on the taste perception threshold of dietary lipids/fats.

As used herein, "agonist" means is a chemical compound that binds or has affinity for the cellular receptors of another drug or natural substance and that produces a stimulatory physiological effect.

The present invention thus provides oleic acid derivative of Formula (Z) or (E)-(I) below comprising a hydrophobic part $C_{17}H_{33}$ linked to a polar head part "A":

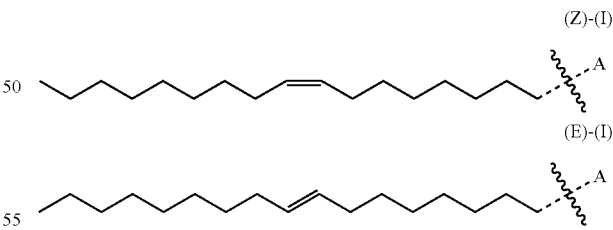

wherein said polar head part A is selected from $A^1$ to $A^4$ below:

-continued

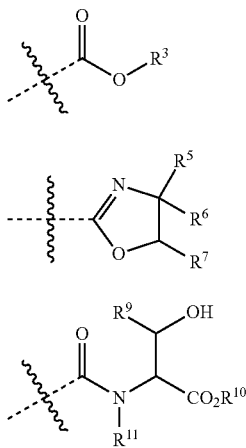

wherein $R^1$ and $R^2$ are independently selected from the group composed of: H or a saturated or unsaturated, straight or branched alkyl group containing 1 to 8 carbon atoms, or $R^1$ and $R^2$ are linked together to form a divalent radical of formula $—R^1-R^2—$, wherein $—R^1-R^2—$ is preferably $—CH_2CH_2—$ or $—(CH_2)_3—$;

with the proviso that:
when $R^1$ or $R^2$=H, respectively $R^2$ or $R^1$ is different from H or from a straight alkyl group containing 2 or 8 carbon atoms, or
when $R^1$ or $R^2$=$—CH_2CH_3$ or $—CH(CH_3)_2$, $R^1$ and $R^2$ are not identical;

$R^3$ is independently selected from the group composed of:

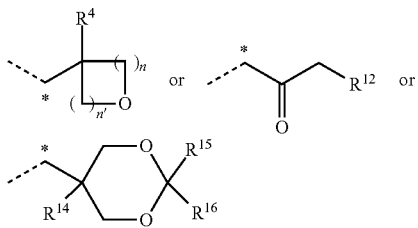

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1 with the proviso that when $R^4$=H, n'≠0; preferably $R^4$ is $CH_3$, "*" is the carbon atom which is attached to the oxygen atom of the $A^2$ polar head;

$R^{12}$ is independently selected from the group composed a saturated or unsaturated, straight or branched alkyl group containing 1 to 4 carbon atoms, or an aromatic group (such as Ph, Tol, Xyl) or $—CO_2R^{13}$ in which $R^{13}$ is a saturated alkyl group containing 1 to 4 carbon atoms;

$R^{14}$, $R^{15}$, $R^{16}$ is independently selected from H or $CH_3$, preferably $R^{14}$=$R^{15}$=$R^{16}$=$CH_3$ or $R^{14}$=H or $CH_3$ and $R^{15}$=$R^{16}$=H;

$R^5$, $R^6$ and $R^7$ are independently selected from the group composed of H or a saturated or unsaturated, straight or branched alkyl group containing 1 to 4 carbon atoms, or $—CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$, preferably $R^5$ and $R^6$, are different from H or $CH_3$;

$R^9$ to $R^{11}$ are independently selected from the group composed of H or a saturated or unsaturated, straight or branched alkyl group containing 1 to 10 carbon atoms, with the proviso that when $R^9$ or $R^{10}$=$CH_3$, respectively $R^{10}$ or $R^9$≠H, preferably $R^9$=H or $CH_3$ and $R^{10}$ is a straight or branched alkyl group containing 2 to 10 carbon atoms;

or a pharmaceutically/food quality acceptable salts thereof.

As used herein, the term "pharmaceutically acceptable salts" refers to salt or complexes that retain the desired biological activity of the above described oleic acid derivatives and exhibit minimal and no undesired toxicological effects. The "pharmaceutically acceptable salts" according to the invention include therapeutically active, non-toxic base or acid salt forms, which the oleic acid derivatives of Formula (I) are able to form.

The term "food quality acceptable salts" used herein also refers to salts or complexes that retain the desired biological activity of the above described oleic acid derivatives and exhibit minimal and no undesired toxicological effects. In addition, the "food quality acceptable salts" according to the invention include cosmetic or non-therapeutic active, non-toxic base or acid salt forms, which the oleic acid derivatives of Formula (I) are able to form. The "food quality acceptable salts" according to the invention also means an edible compound, which is able to be eaten/ingested by an individual without any risk to his health. "Edible" used herein a consumable product, which can be eaten or ingested by the individual (advantageously a human or animal subject) without any risk to his health.

The use of these oleic acid derivatives of formula (I) enables to contribute to curtailed dietary fat intake and, consequently, help combat pathologies, associated with weight disorders or dyslipidemia, such as obesity and obesity-associated type 2 diabetes, etc.

Hence, in other aspect, the invention relates to oleic acid derivative of Formula (I) below comprising a hydrophobic part $C_{17}H_{33}$ (Z or E) linked to a polar head part "A":

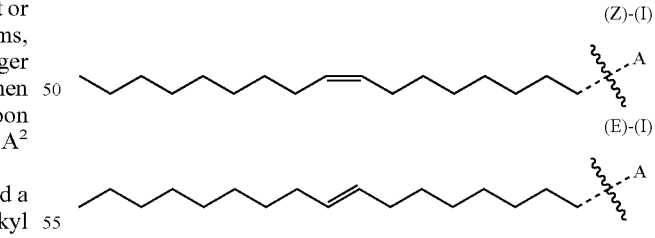

wherein said polar head part A is selected from $A^1$ to $A^4$ below:

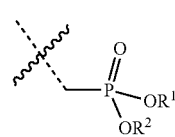

-continued

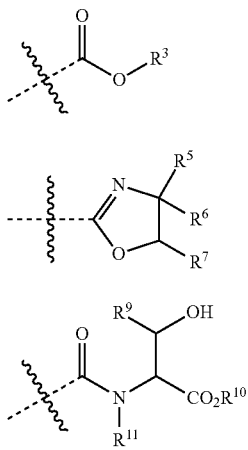

wherein
$R^1$ and $R^2$ are independently selected from the group composed of H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —$CH_2CH_2$— or —$(CH_2)_3$—;
$R^3$ is independently selected from the group composed of:

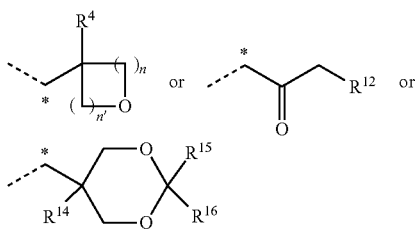

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1, preferably with the proviso that when $R^4$=H, n'≠0 and n≠1; "*" is the carbon atom which is attached to the oxygen atom of the $A^2$ polar head;
$R^{12}$ is independently selected from the group composed from H or an alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms,
$R^{14}$, $R^{15}$, $R^{16}$ is independently selected from H or $CH_3$, preferably $R^{14}$=$R^{15}$=$R^{16}$=$CH_3$; or $R^{14}$=H or $CH_3$ and $R^{15}$=$R^{16}$=H; $R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms;
$R^9$ to $R^{11}$ are independently selected from the group composed of H or a saturated or unsaturated, straight or branched alkyl group containing 1 to 10 carbon atoms, preferably from 2 to 10 carbon atoms;
or a pharmaceutically/food quality acceptable salts thereof,
for use as a medicament.

The invention also refers to a pharmaceutical composition comprising, at least one pharmaceutically acceptable carrier and at least one oleic acid derivative such as described above for the use as a medicament.

In addition, the present invention also refers to the oleic acid derivatives defined above for the use as a medicament or the pharmaceutical composition as described above for the use in the treatment of a disorder modulated by the GPR120 receptor and/or the CD36 receptor, comprising administering to a subject in need thereof a therapeutically effective amount of said oleic acid derivative or of said pharmaceutical composition.

When used in the therapeutic treatment of excess weight, excess body fat, the oleic acid derivatives according to the invention especially aim at people who are stressed or anxious, and/or having a diet with a high fat, and/or a sedentary lifestyle, and/or suffering from hormonal imbalances and/or from a genetic susceptibility to excess weight and/or obesity, and/or taking prescription drugs which can cause weight gain and/or being "hyposensitive" to detect dietary fatty acid due to, for instance, the genetic polymorphism of the CD36 and/or GPR120 genes which is different from the one of lean people.

In addition, the oleic acid derivatives according to the invention such as described above as such or for the use as medicament may be used in food composition or as cosmetic treatment (i.e. non-therapeutic treatment) in lean or healthy people so as to improve their appearance.

Hence, in another aspect, the present invention relates to a food composition comprising, at least one food ingredient and/or at least one food additive and at least one oleic acid derivative such as described above.

The invention also refers to a cosmetic use/non-therapeutic use of the oleic acid derivatives such as described above or of the food composition such as described above, as taste enhancer, as taste modulator, or as appetite suppressant.

Such a cosmetic treatment is aimed at individuals whose weight and excess fat are not associated with a growing burden of disease and in particular at individuals who do not suffer from glucose metabolic disorders, insulin resistance, any metabolic syndrome, diabetes or vascular disorders.

The various embodiments of the present invention are especially described in the detailed specification hereafter. These embodiments may be considered separately or be combined with each other.

DETAILED DESCRIPTION OF THE INVENTION AND PREFERRED EMBODIMENTS

The terms "comprise" (and any grammatical variation thereof, such as "comprises" and "comprising"), "compose" (and any grammatical variation thereof, such as "composed of), "have" (and any grammatical variation thereof, such as "has" and "having"), "contain" (and any grammatical variation thereof, such as "contains" and "containing"), and "include" (and any grammatical variation thereof, such as "includes" and "including") are open-ended linking verbs. They are used to specify the presence of stated features, integers, steps or components or groups thereof, but do not preclude the presence or addition of one or more other features, integers, steps or components or groups thereof. As a result, a method, or a step in a method, that "comprises," "compose", "has," "contains," or "includes" one or more steps or elements possesses those one or more steps or elements, but is not limited to possessing only those one or more steps or elements. In specific embodiments of the invention, each of these open-ended linking verbs can be independently interpreted as meaning "consisting of".

Unless otherwise indicated, all numbers or expressions referring to quantities of ingredients, ranges, reaction conditions, etc. used herein are to be understood as modified in all instances by the term "about."

Also unless otherwise indicated, the indication of an interval of values «from X to Y» or "between X to Y", according to the present invention, means as including the values of X and Y.

Oleic Acid Derivatives According to the Invention (FAA Compounds)

As previously mentioned, the present invention relates to oleic acid derivative of Formula (Z)- or (E)-(I) below comprising a hydrophobic part $C_{17}H_{33}$ linked to a polar head part "A":

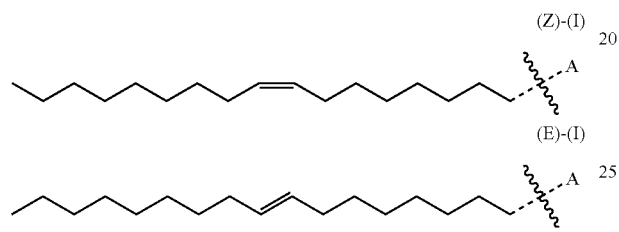

(Z)-(I)

(E)-(I)

wherein said polar head part A is selected from $A^1$ to $A^4$ below:

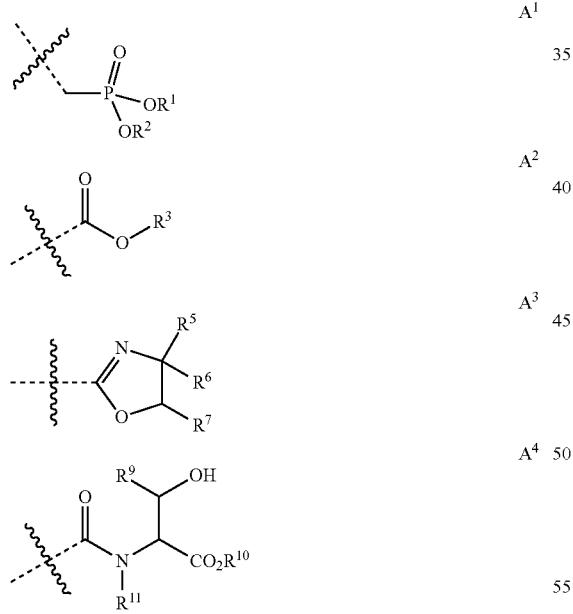

$A^1$ $A^2$ $A^3$ $A^4$ wherein $R^1$ and $R^2$ are independently selected from the group composed of: H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —$CH_2CH_2$— or —$(CH_2)_3$—; with the proviso that:

when $R^1$ or $R^2$=H, respectively $R^2$ or $R^1$ is different from H or from a straight alkyl group containing 2 or 8 carbon atoms, or when $R^1$ or $R^2$=—$CH_2CH_3$ or —$CH(CH_3)_2$, $R^1$ and $R^2$ are not identical;

$R^3$ is independently selected from the group composed of:

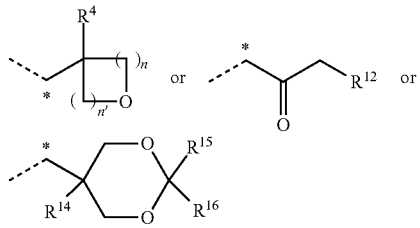

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1 with the proviso that when $R^4$=H, n'≠0; preferably $R^4$ is $CH_3$, "*" is the carbon atom which is attached to the oxygen atom of the $A^2$ polar head;

$R^{12}$ is independently selected from the group composed a saturated or unsaturated, straight or branched alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms;

$R^{14}$, $R^{15}$, $R^{16}$ is independently selected from H or $CH_3$, preferably $R^{14}$=$R^{15}$=$R^{16}$=$CH_3$ or $R^{14}$=H or $CH_3$ and $R^{15}$=$R^{16}$=H;

$R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$, preferably $R^5$ and $R^6$, are different from H or $CH_3$;

$R^9$ to $R^{11}$ are independently selected from the group composed of H or a saturated or unsaturated, straight or branched alkyl group containing 1 to 10 carbon atoms, with the proviso that when $R^9$ or $R^{10}$=$CH_3$, respectively $R^{10}$ or $R^9$≠H, preferably $R^9$=H or $CH_3$ and $R^{10}$ is a straight or branched alkyl group containing 2 to 10 carbon atoms;

or a pharmaceutically/food quality acceptable salts thereof.

Hereafter, the oleic acid derivatives of formula (I) according to the invention are also called "FAA compounds".

In addition, the FAA compounds according to the invention are considered as GRAS (Generally Recognized As Safe) since they derive from naturally available dietary fatty acid, i.e. oleic acid (OA) of Formula (II) below.

Formula (II)

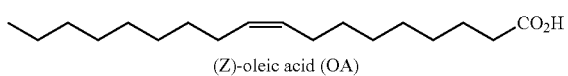

(Z)-oleic acid (OA)

Indeed, the hydrophobic part of all the FAA compounds according to the invention is identical ($C_{17}H_{33}$) to the one of the OA compound: the carbon-length or the methyl-terminal of OA has not been changed or amended to form the FAA compounds according to the invention. Only, the carboxylic (—$CO_2H$) terminal part has been changed by different prosthetic groups forming the polar head part A of the FAA compounds, called hereafter $A^1$ to $A^4$.

Thus, the different FAA compounds according to the invention all share a significant structural element, which is a common chemical structure which occupies a large portion of their structures, that is to say: the hydrophobic part $C_{17}H_{33}$. Moreover, according to the present invention, the FAA compound may have a molecular weight which is close to the one of the oleic acid, that is to say close to 282.46 g/mol. Especially, the FAA compound according to the invention has a molecular weight ranging from about 280 to about 600 g/mol, preferably ranging from 300 to 600 g/mol, in particular ranging from about from 330 to 460 g/mol.

According to the invention, "a molecular weight ranging from about 280 to about 600 g/mol" comprises the followings values: 280; 290; 300; 310; 320; 330; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399; 400; 410; 420; 430; 440; 450; 460; 470; 480; 490; 500; 510; 520; 530; 540; 550; 560; 570; 580; 590; 600 and all intervals included between these values.

In general, these FAA compounds are synthesized from oleic acid, typically technical oleic acid.

In addition, as it will be described below in the Example part, all these different FAA compounds have a common property. Indeed, they are able to bind to fast taste receptors, such as CD36 and/or GPR120.

Therefore, these different FAA compounds according to the invention have similar nature and hence form a single invention.

The compounds with the polar head $A^1$-$A^4$ of the invention are derived from oleic acid (OA) (Scheme 1 below).

Their synthesis is based either on the condensation of oleic acid with alcohols $R^3OH$, β-amino alcohols or β-hydroxyamino esters to afford the compounds with the polar head $A^2$, $A^3$ or $A^4$, respectively (Scheme 1a-c). On the other hand, the $A^1$-based compounds were synthesized by alkylation of dialkylphosphite [$HP(O(OR^1)(OR^2)$] with the octadec-9-en-1-yl-bromide ($C_{18}H_{35}Br$) previously prepared from OA by subsequent reduction and halogenation reactions (Scheme 1d). Experimental parts are reported for all compounds in the example part below.

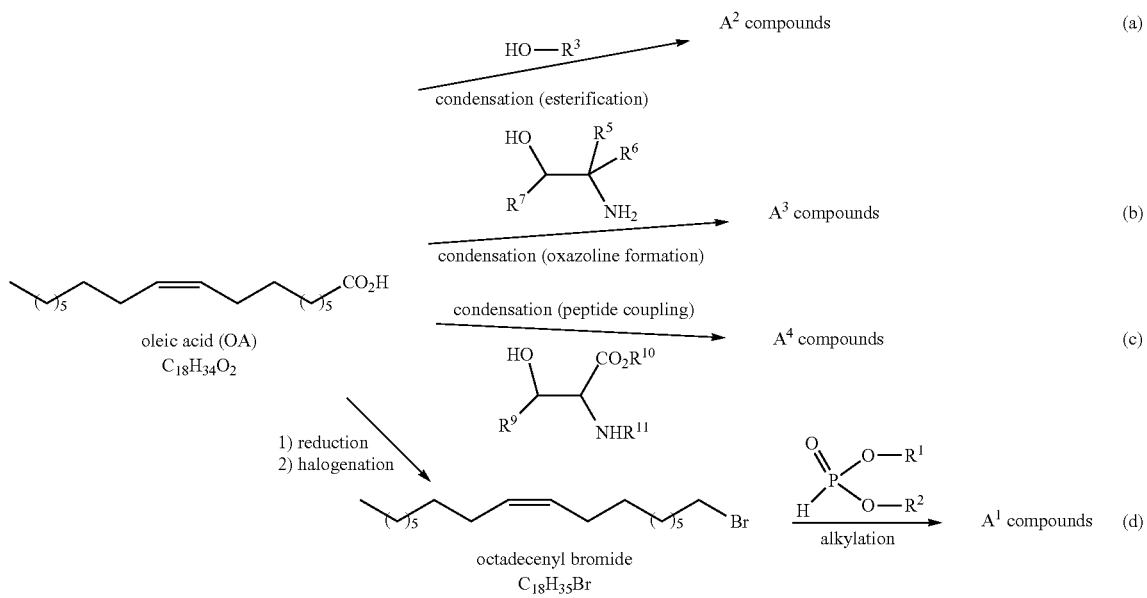

Scheme 1

According to a first embodiment of the invention, the polar head "A" of the FAA compound has a phosphorus group and may be selected from the group $A^1$:

$A^1$ wherein $R^1$ and $R^2$ are independently selected from the group composed of: H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —$CH_2CH_2$— or —$(CH_2)_3$—;
with the proviso that:
when $R^1$ or $R^2$=H, respectively $R^2$ or $R^1$ is different from H or from a straight alkyl group containing 2 or 8 carbon atoms, or
when $R^1$ or $R^2$=—$CH_2CH_3$ or —$CH(CH_3)_2$, $R^1$ and $R^2$ are not identical.

In general, $R^1$ and $R^2$ may be independently selected from the group composed of methyl, or a saturated or unsaturated, straight or branched alkyl group containing 4 to 6 carbon atoms, or $R^1$ and $R^2$ are linked together by a bridge of formula —$R^1$-$R^2$—, wherein —$R^1$-$R^2$— is preferably —$(CH_2)_2$— or —$(CH_2)_3$, or a pharmaceutically/food quality acceptable salts thereof.

Advantageously, $R^1$ and $R^2$ are different of the following combinations:

TABLE I

| $R^1$ | H | —$CH_2CH_3$ | H | $CH_2CH_3$ | —$CH(CH_3)_2$ | H | —$(CH_2)_7CH_3$ |
|---|---|---|---|---|---|---|---|
| $R^2$ | H | —$CH_2CH_3$ | —$CH_2CH_3$ | H | —$CH(CH_3)_2$ | —$(CH_2)_7CH_3$ | H |

Typically, $R^1$ and $R^2$ are linked together so that —$R^1$-$R^2$— is —$(CH_2)_3$ and form the following compound of Formula (III)

Formula (III)

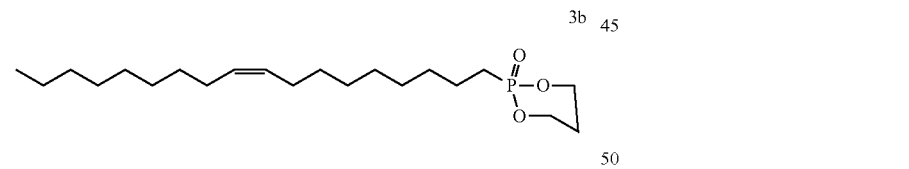

According to this embodiment, $R^1$ and $R^2$ of $A^1$ may be butyl group, preferably a linear butyl group, so as to form the compound responding to the formula (IV) below:

Formula (IV)

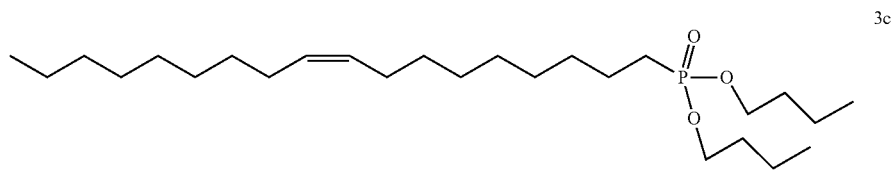

These differents FAA organophosphorus compounds may be prepared from oleic acid (OA) by alkylation of dialkylphosphite derivative 1a with the octadec-9-en-1-yl-bromide previously prepared by subsequent reduction of OA with $LiAlH_4$ then bromation using a mixture $PPh_3/CBr_4$ (Scheme 2).

Scheme 2

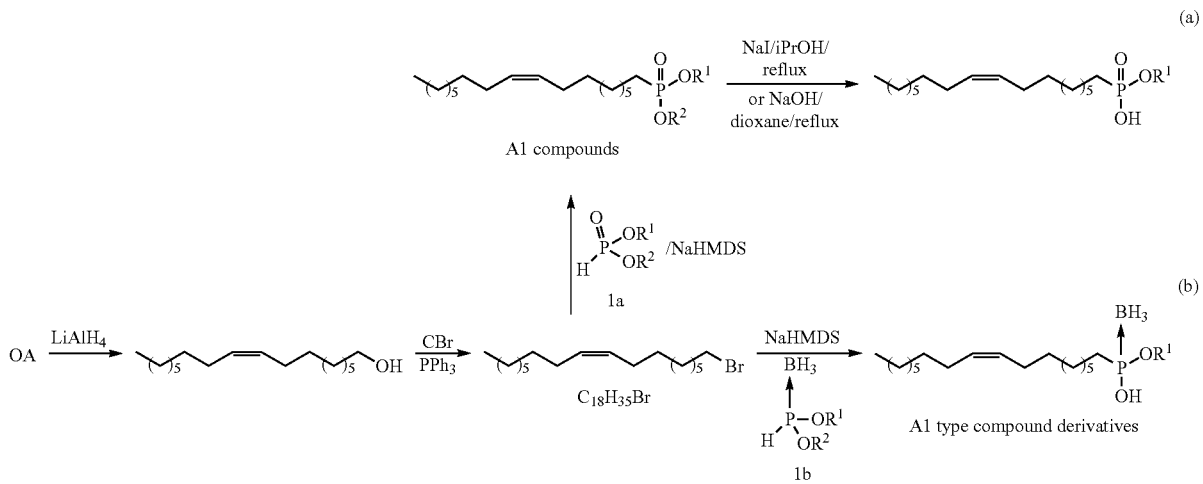

It should be noted that the $A^1$ compounds could be saponified by heating at reflux a mixture of NaI in isopropanol or NaOH in dioxane, to afford the corresponding $A^1$-based derivative as a mono acid phosphonic: i.e. bearing a $-P(O)(OR^1)OH$ as polar group (Scheme 2a).

In addition, FAA organophosphorus $A^1$-based compounds must also be prepared by alkylation of the dialkylphosphonous borane complex 1b with the bromide ($C_{18}H_{35}Br$) derived from OA (Scheme 2b).

Moreover, the synthesis of $A^1$-based derivatives has been envisaged by keeping in consideration that a FAA should be isosteric (function as an ester) in the hydrolysis transition state inside the receptor site.

In particular, the FAA compounds according to the invention may correspond to compound 3b, compound 3c, such as described above or a mixture thereof.

According to a second embodiment of the invention, the polar head "A" of the FAA compound may be selected from the group $A^2$:

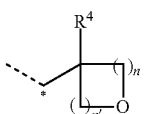

$A^2$ $R^3$ is independently selected from the group composed of:

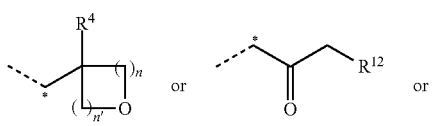

-continued

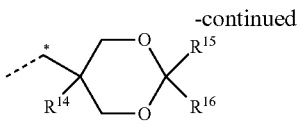

wherein $R^4$, $R^{12}$ and $R^{14}$, $R^{15}$, $R^{16}$ are such as defined above.

According to a preferred first aspect of this embodiment of $A^2$, $R^3$ is an oxacycloalkane group according to the formula below:

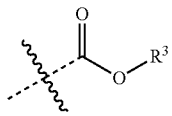

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1 with the proviso that when $R^4$=H, n'≠0; preferably $R^4$ is a straight or branched alkyl group containing 1 to 4 carbon atoms, "*" is the carbon atom which is attached to the oxygen atom of the $A^2$ polar head, a pharmaceutically/food quality acceptable salts thereof.

In general, according to this embodiment, $R^4$ may be a straight or branched alkyl group containing 1 to 4 carbon atoms and may be typically $CH_3$.

For instance, the followings compounds or a pharmaceutically/food quality acceptable salts thereof are convenient according to the invention:

TABLE II

| Compound | Formula | R⁴ | n | n' | Structure |
|---|---|---|---|---|---|
| (Z)-2a (17FM016) | (V) | CH₃ | 1 | 1 | 2a |
| (E)-2b (17FM020) | (V) | CH₃ | 1 | 1 | 2b |
| (Z)-2d (18FM094) | (VII) | H | 2 | 1 | 2d |
| (Z)-2e (17FM057) | (VIII) | H | 1 | 1 | 2e |
| (Z) or (E)-2k | | CH₃ | 1 | 0 | 2k |
| (Z) or (E)-2l | | H | 3 | 1 | 2l |
| (Z) or (E)-2m | | H | 2 | 2 | 2m |

In particular, the FAA compounds according to the invention may correspond to compounds 2a, 2b, 2d, 2e, 2k, 2l, 2m such as described above, or a mixture thereof and correspond typically to compounds 2a, 2b, 2e, 2k, 2l, 2m or a mixture thereof (i.e.: according to this specific embodiment, $R^4 \neq H$, $n \neq 2$ and $n' \neq 1$).

Advantageously, $R^4$, n and n' are different of the following combinations:

TABLE III

| $R^4$ | H | H | H |
|---|---|---|---|
| n | 1 | 3 | 4 |
| n' | 0 | 0 | 0 |

According to a preferred second aspect of this embodiment relating to the polar head $A^2$, $R^3$ may be an alpha-hydroxyketone group:

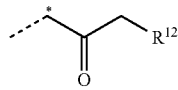

and $R^{12}$ is independently selected from the group composed a saturated or unsaturated, straight or branched alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms, or a pharmaceutically/food quality acceptable salts thereof.

Especially, $R^{12}$ is different from H, or a pharmaceutically/food quality acceptable salts thereof.

According to a preferred third aspect of this embodiment relating to the polar head $A^2$, $R^3$ may be:

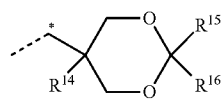

in which $R^{14}$, $R^{15}$, $R^{16}$ is independently selected from H or $CH_3$, preferably $R^{14}=R^{15}=R^{16}=CH_3$ or $R^{14}=H$ or $CH_3$ and $R^{15}=R^{16}=H$;

or a pharmaceutically/food quality acceptable salts thereof.

For instance, the FAA compound according to this embodiment may correspond to the formula (XI) below:

Formula (XI)

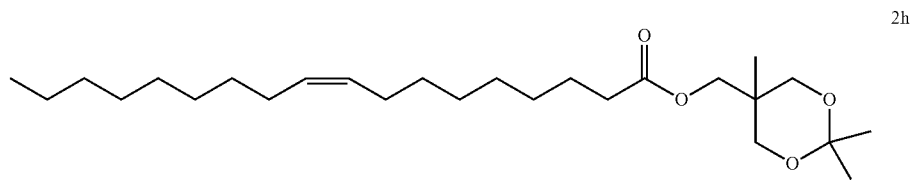

2h

According to a third embodiment of the invention, the polar head "A" of the FAA compound may be selected from the group $A^3$:

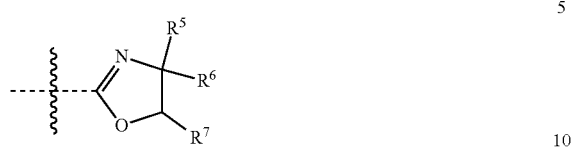

wherein $R^5$, $R^6$ and $R^7$ are independently selected from the group composed of H or a saturated or unsaturated, straight or branched alkyl group containing 1 to 4 carbon atoms, or $-CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$, preferably $R^5$ and $R^6$, are different from H or $CH_3$, or a pharmaceutically/food quality acceptable salts thereof.

Advantageously, $R^5$, $R^6$ and $R^7$ are different of the following combinations:

TABLE IV

| | | | | |
|---|---|---|---|---|
| $R^5$ | H | $CH_3$ | $CH_3$ | H |
| $R^6$ | H | H | $CH_3$ | H |
| $R^7$ | H | H | H | $CH_3$ |

Especially in this embodiment, $R^5$ may be H, $R^6$ may be $-CO_2Et$ and $R^7$ may be H, or a pharmaceutically/food quality acceptable salts thereof, so as to form the FAA compound of Formula (XII) below:

Formula (XII)

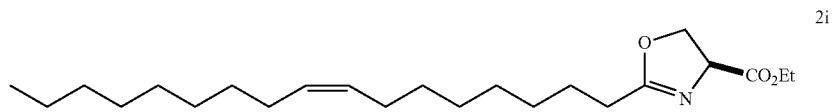

According to a fourth embodiment of the invention, the polar head "A" of the FAA compound may be selected from the group $A^4$:

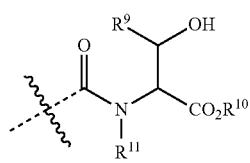

wherein $R^9$ to $R^{11}$ are independently selected from the group composed of H or a saturated or unsaturated, straight or branched alkyl group containing 1 to 10 carbon atoms, with the proviso that when $R^9$ or $R^{10}=CH_3$, respectively $R^{10}$ or $R^9 \neq H$, preferably $R^9=H$ or $CH_3$ and $R^{10}$ is a straight or branched alkyl group containing 2 to 10 carbon atoms, or a pharmaceutically/food quality acceptable salts thereof.

In particular, $R^9$ may be H or $CH_3$ and $R^{10}$ may be a straight or branched alkyl group containing 2 to 10 carbon atoms.

For instance, $R^9$ may be H, $R^{10}$ may be an ethyl group (Et) and $R^{11}$ may be H, and may correspond to the formula (XIII) below:

Formula (XIII)

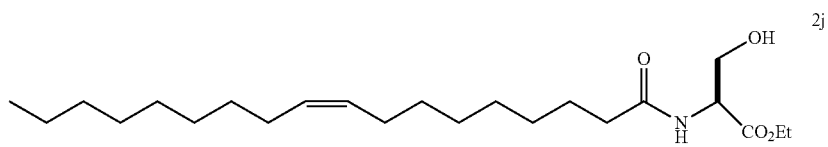

Advantageously, $R^9$, $R^{10}$ and $R^{11}$ are different of the following combinations:

TABLE V

| $R^9$ | $CH_3$ | H |
|---|---|---|
| $R^{10}$ | H | $CH_3$ |
| $R^{11}$ | H | H |

The FAA compounds of formula (XIII) and (XII) may be prepared by reaction of oleic acid (OA) with a beta-hydroxy-alpha-aminoester 4 using a coupling agent such as DCC/HOBt or PyBOP (see for example *J. Med. Chem.* 2009, 4358), and then internal condensation using a dehydrating agent such as deoxofluor (see *Tetrahedron Lett.* 2005, 8917 and 2006, 6497), respectively (Scheme 3).

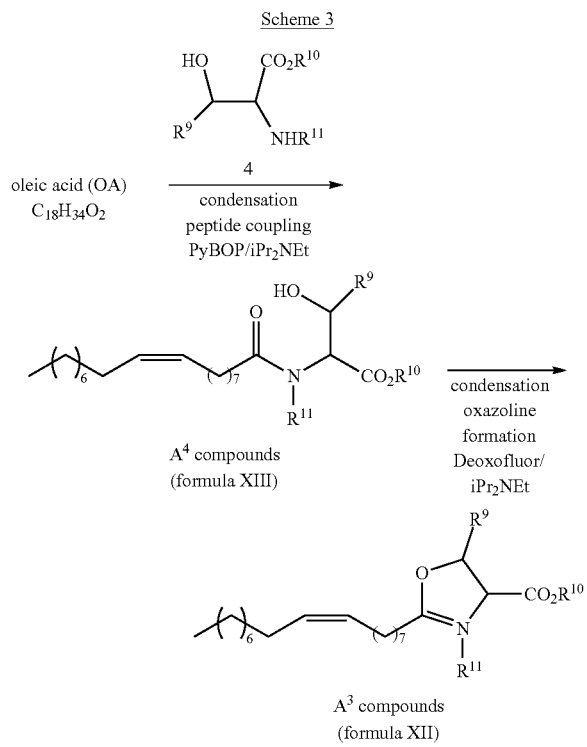

The synthesis of compounds such as $A^2$ to $A^4$ type from oleic acid has been carried out, by employing protective reagents well-tolerated by the organism such as alcohols, aminoalcohols, or hydroxyamino esters, with the aim of obtaining derivatives or metabolites presenting no risk to health. Their synthesis is based either on the condensation of oleic acid with alcohols $R^3OH$, β-amino alcohols or β-hydroxyamino esters to afford the compounds $A^2$, $A^3$ or $A^4$, respectively (Scheme 1).

In particular, the FAA compound according to the invention is selected from compound of Formula (III) to (XIII), or combination thereof and is especially compound of formula (Z)-(V).

The FAA compound may be in a great plurality galenic form, such in a liquid form or in the form of a capsule, dragee, pill, powder, suppository, or any other galenic formulation.

Human and Animal Pharmaceutical Composition According to the Invention

As previously mentioned, these FAA compounds described above, once in the mouth cavity of an individual or an animal, advantageously would trigger fat-like taste and can be used to reduce fat contents in the diet.

Especially, the Applicant has surprisingly discovered that these specific FAA compounds are able to target the lingual fat taste receptors CD36 and/or GPR120 (in general both CD36 and GPR120) involved in the gustatory perception of dietary lipids. In addition, the Applicant has also discovered that these compounds possess fat-like taste. Besides, the Applicant also observed that at least two FAA compounds, i.e., compound 2a (17FM016) and compound 3a (17FM026) tested below, triggered attraction in mice, in a two-bottle preference test, at 102 times higher concentrations than OA which was preferred by these animals at 7.7 mM (see FIG. 4 and FIG. 5). Indeed, FAA compounds exhibit a high or the same affinity as natural fatty acids, such as oleic acid and bind strongly to taste receptors and, consequently, trigger fat-like taste without any or very few caloric value.

In support of that view, freshly isolated and primary cultured mice type II taste bud cells (expressing GPR120 and CD36) are used. These cells also express functional receptors of other five taste modalities (bitter, sweet, salt, acid, umami). It has been demonstrated that at least two of the FAA compounds according to the invention are biologically active. One compound termed as 2a bounds to CD36 (FIG. 1B), whereas the other 3a acts both to CD36 and GPR120 (FIG. 2B and FIG. 3). These two compounds, in mouse taste bud cells, induce, similar to oleic acid (OA), a rapid and significant rise in calcium signaling, considered as one of the earliest events in taste perception (FIG. 1A and FIG. 2A). These two compounds also trigger a "taste-like" sensation in a two-bottle preference test in mice (FIG. 4 and FIG. 5).

As it will be described below, the FAA compounds according to the invention may be used to decrease circulating lipids in other pathophysiological situations. It is noteworthy that a reduction in the consumption of products rich in saturated fatty acids is advised to the subjects, suffering from obesity or the pathologies related to dyslipidemia, such as atherosclerosis, hypertension, diabetes type II, etc.

Therefore, the invention also refers to oleic acid derivatives of Formula (I) below comprising a hydrophobic part $C_{17}H_{33}$ (Z or E) linked to a polar head part "A":

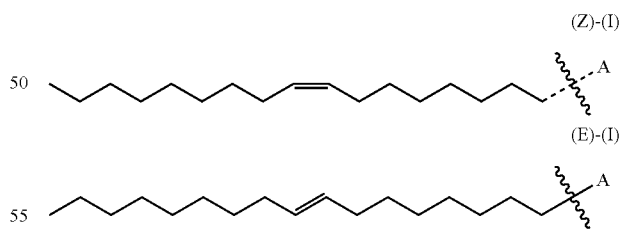

wherein said polar head part A is selected from $A^1$ to $A^4$ below:

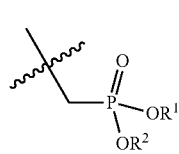

-continued

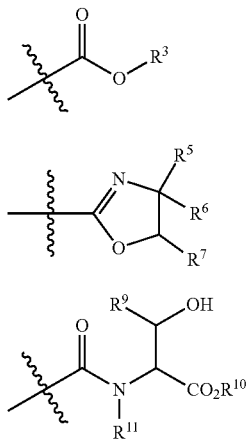

wherein R¹ and R² are independently selected from the group composed of H or a saturated or unsaturated, straight or branched alkyl group containing 1 to 8 carbon atoms, or R¹ and R² are linked together to form a divalent radical of formula —R¹-R²—, R³ is independently selected from the group composed of:

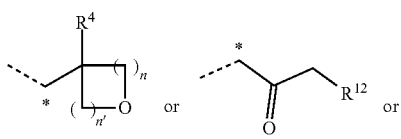

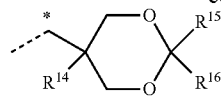

wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1, preferably with the proviso that when $R^4$=H, n'≠0 and n≠1; "*" is the carbon atom which is attached to the oxygen atom of the $A^2$ polar head;

$R^{12}$ is independently selected from the group composed from H or an alkyl group containing 1 to 4 carbon atoms, or an aromatic group (such as Ph, Tol, Xyl) or —$CO_2R^{13}$ in which $R^{13}$ is a saturated alkyl group containing 1 to 4 carbon atoms, $R^{14}$, $R^{15}$, $R^{16}$ is independently selected from H or $CH_3$, preferably $R^{14}$=$R^{15}$=$R^{16}$=$CH_3$; or $R^{14}$=H or $CH_3$ and $R^{15}$=$R^{16}$=H; $R^5$, $R^6$ and $R^7$ are independently selected from the group composed of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms;

$R^9$ to $R^{11}$ are independently selected from the group composed of H or a saturated or unsaturated, straight or branched alkyl group containing 1 to 10 carbon atoms, preferably from 2 to 10 carbon atoms;

or a pharmaceutically/food quality acceptable salts thereof, for use as a medicament.

TABLE VI

For instance, the followings compounds or a pharmaceutically/food quality acceptable salts thereof are convenient for the pharmaceutical composition according to the invention: A¹

| Compound | Formula | R¹ | R² | Structure |
|---|---|---|---|---|
| 3a (17FM026) | (XIV) | —$CH_2CH_3$ | —$CH_2CH_3$ | 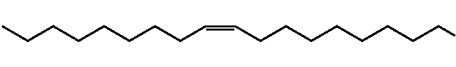 3a |
| 3b | (III) | —$(CH_2)_3$— | |  3b |
| 3c (18FM110) | (IV) | —$(CH_2)_3CH_3$ | —$(CH_2)_3CH_3$ |  3c |

TABLE VII

| Compound | Formula | R⁴ | n | n' | Structure |
|---|---|---|---|---|---|
| (Z)-2a (17FM016) | (Z)-(V) | CH₃ | 1 | 1 | 2a |
| (E)-2b (17FM020) | (E)-(V) | CH₃ | 1 | 1 | 2b |
| (Z)-2c (17FM060) | (VI) | H | 3 | 0 | 2c |
| (Z)-2d (18FM094) | (VII) | H | 2 | 1 | 2d |
| (Z)-2e (17FM057) | (VIII) | H | 1 | 1 | 2e |
| (Z)-2f (17FM066) | (IX) | H | 1 | 0 | 2f |

TABLE VIII

| Compound | Formula | R¹² | Structure |
|---|---|---|---|
| (Z)-2g (17FM064) | (X) | H | 2g |

TABLE IX

A²

| Compound | Formula | Structure |
|---|---|---|
| (Z)-2h (17FM058) | (XI) — — — | ![structure 2h] |

2h

TABLE X

A³

| Compound | Formula | R⁵ | R⁶ | R⁷ | Structure |
|---|---|---|---|---|---|
| (Z)-2i (18FM100) | (XII) | H | —CO$_2$Et | H | ![structure] |

TABLE XI

A4

| Compound | Formula | R⁹ | R¹⁰ | R¹¹ | Structure |
|---|---|---|---|---|---|
| (Z)-2j (18FM099) | (XIII) | H | Et | H | ![structure 2j] |

2j

In general, the substituents $R^1$ to $R^{16}$ may be such as defined above for the oleic acid derivatives. Of course, all the characteristics of the oleic acid derivatives may be convenient for the following description of the pharmaceutical composition according to the invention.

For instance, according to an embodiment of the invention, $R^1$ and $R^2$ are independently selected from the group composed of: H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is preferably —CH$_2$CH$_2$— or —(CH$_2$)$_3$—;

with the proviso that:
- when $R^1$ or $R^2$=H, respectively $R^2$ or $R^1$ is different from H or from a straight alkyl group containing 2 or 8 carbon atoms, or
- when $R^1$ or $R^2$=—CH$_2$CH$_3$ or —CH(CH$_3$)$_2$ or optionally —(CH$_2$)$_3$CH$_3$, $R^1$ and $R^2$ are not identical;

$R^3$ is independently selected from the group composed of:

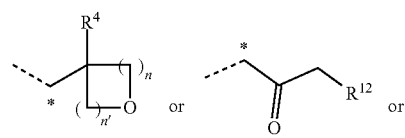

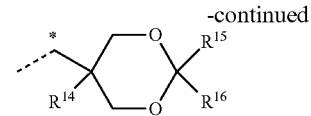

-continued wherein $R^4$ is independently selected from the group composed of H or a saturated or unsaturated, straight or branched alkyl group containing 1 to 4 carbon atoms, n is an integer selected from 1 to 4, and n' is an integer that is equal to 0 or 1 with the proviso that when $R^4$=H, n'≠0; preferably $R^4$ is CH$_3$, "*" is the carbon atom which is attached to the oxygen atom of the A² polar head;

$R^{12}$ is independently selected from the group composed of a saturated or unsaturated, straight or branched alkyl group containing 1 to 4 carbon atoms, or an aromatic group (such as Ph, Tol, Xyl) or —CO$_2$R$^{13}$ in which $R^{13}$ is a saturated alkyl group containing 1 to 4 carbon atoms;

$R^{14}$, $R^{15}$, $R^{16}$ is independently selected from H or CH$_3$, preferably $R^{14}$=$R^{15}$=$R^{16}$=CH$_3$ or $R^{14}$=H or CH$_3$ and $R^{15}$=$R^{16}$=H;

$R^5$, $R^6$ and $R^7$ are independently selected from the group composed of H or a saturated or unsaturated, straight or branched alkyl group containing 1 to 4 carbon atoms, or —CO$_2$R$^8$ in which $R^8$ is a saturated or unsaturated, straight or branched alkyl group containing 1 to 4 carbon atoms, with the proviso that when $R^7$ is H or CH$_3$, at least one of $R^5$ and $R^6$, preferably $R^5$ and $R^6$, are different from H or CH$_3$;

$R^9$ to $R^{11}$ are independently selected from the group composed of H or a saturated or unsaturated, straight or branched alkyl group containing 1 to 10 carbon atoms, with the proviso that when $R^9$ or $R^{10}$=$CH_3$, respectively $R^{10}$ or $R^9 \neq H$, preferably $R^9$=H or $CH_3$ and $R^{10}$ is a straight or branched alkyl group containing 2 to 10 carbon atoms;

or a pharmaceutically/food quality acceptable salts thereof.

According to the first aspect, a pharmaceutical composition according to the present invention comprises as active compound at least one oleic acid derivative (FAA compound) such as described above or one pharmaceutically salt thereof, in an amount suitable for treating a disorder modulated by the GPR120 receptor and/or the CD36 fat taste receptor in individuals in need of such treatment.

In general, the disorder modulated by the GPR120 receptor and/or the CD36 receptor is selected from the group consisting of: diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, body weight disorder, fatty liver disease, dyslipidemia, hyperlipidemia, hypertriglyceridemia, hypercholesterolemia, low high-density lipoprotein (HDL), high low-density lipoprotein (LDL), lipid disorders and liver diseases such as NASH (Non-Alcoholic SteatoHepatitis), NAFLD (Non-Alcoholic Fatty Liver Disease) and liver cirrhosis, dyslipidemia, artherosclerosis and cachexia.

The Applicant considers that a significant reduction of lipids can be envisaged by using FAA compounds according to the invention. A reduction in lipids, even of 25% in human daily diet, would be beneficial for instance for pathological dyslipidemia.

According to the second aspect, a pharmaceutical composition according to the present invention is useful as agonist of fat taste receptor GPR120 and/or CD36.

According to the third aspect, a pharmaceutical composition according to the present invention is useful as appetite suppressant.

Preferably, a FAA compound of the invention or the pharmaceutical composition is administered by mouth (oral administration).

Suitable forms for oral route are for example tablets, hard gelatin capsules, lozenges, powders, granules, lyophilizates, oral solutions and syrups. Tablets, powders, granules, lyophilizates, oral solutions and syrups represent the currently most preferred pharmaceutical or cosmetic form adapted to oral administration. If a solid composition in the form of tablets should be prepared, it would be possible for example to combine the FAA compound with a physiologically acceptable vehicle such as gelatin, starch, lactose, magnesium stearate, talc, gum arabic or equivalents. Tablets may be of various types, providing an immediate release, or a controlled or a slow release, and optionally be in an effervescent or oro-dispersible form. Gelatin capsules may be obtained by combining the FAA compound with a diluent and pouring the resulting mixture into soft or hard capsules.

A preparation in the form of syrup or elixir may for example contain the FAA compound with a suitable sweetener, antiseptic agent, preservative, flavoring agent or coloring agent.

Powders, lyophilizates or granules that are dispersible in water may contain the FAA compound in admixture with dispersing agents or wetting agents or suspending agents, as well as with taste modifiers or sweeteners.

In its form suitable for human administration, a pharmaceutical composition according to the present invention advantageously comprises at least one FAA compound or one pharmaceutically salt thereof in an amount suitable for a daily administration of the active compound.

In its form suitable for animal administration, a pharmaceutical composition according to the present invention comprises FAA compound in an amount suitable for a daily administration.

A pharmaceutical composition according to the present invention comprises FAA compound in association with at least one excipient selected from the pharmaceutically acceptable excipients.

Physiologically acceptable adjuvants, vehicles and excipients are also described in "*Handbook of Pharmaceutical Excipients*", $2^{nd}$ edition, American Pharmaceutical Association, 1994.

To formulate a pharmaceutical composition according to the present invention, the man skilled in the art will advantageously refer to the last edition of the European Pharmacopoeia or the American Pharmacopoeia (USP).

Food Composition

As previously mentioned, such FAA compounds according to the invention such as defined for the pharmaceutical composition could also be used within the framework of a cosmetic use (or method) in the form of a food composition in people who are in good health, that is to say whose weight and/or excess body fat are not associated with a growing burden of disease.

As used herein, "people in good health" preferably mean individuals who have a corpulence considered as normal according to the WHO standards. When used with a cosmetic approach, said FAA compound of the invention will preferably be proposed in a form that is adapted to oral administration, as for example a food supplement or a functional food.

The present invention also relates food composition comprising, at least one food ingredient and/or at least one food additive and at least one FAA compound such as described above.

Of course, the characteristics of the oleic acid derivatives described above and of the pharmaceutic composition are here included for the description of the food composition.

In a first aspect of the invention for instance as supplement food, the food composition according to the present invention comes is in different galenic form, such as liquid form or in the form of a capsule, dragee, pill, powder, suppository, or any other galenic formulation.

As used herein, a "food supplement" means a preparation that is intended to supply a nutrient that is missing from a diet, and here especially, which may replace natural fatty acid.

In a second aspect of the invention, for instance as functional food, the food composition according to the present invention comes is in a great plurality of food and beverage forms, comprising juices (fruits or vegetables), oils, butters, margarines, vegetal fats, cans (for example tuna fish in oil), soups, milk-based preparations (yogurts, cottage cheese), ice creams, cheeses (for example oil-kept cheeses), baked products (such as bread, cookies and cakes), puddings, confectionary products, cereal bars, breakfast cereals, condiments, seasoning products (especially spices and dressings).

As used herein, a "functional food" is intended to mean any food or beverage, for example, milk products from animal origin (butter, cheese, yogurt, milk) or from vegetable origin (milk, yogurt, cereals, fruit or vegetable juices, soups, etc.) to which a combination product of the invention has been added. Preferably, said FAA compound then comes as a single composition added to food, as previously mentioned.

Generally, the food composition according to the present invention comes as any form, and in particular fat-base food products (butter, oil, margarine), bread, cookies, or oil kept food products, such as cheese, fish, meat, vegetables, or salads) or as seasoning products, such as condiments.

Preferably, a food composition according to the present invention comprises the FAA compound or one salt thereof in an amount suitable for a daily oral administration.

For human supply, a food composition according to the present invention comprises an amount of active compound suitable for a daily supply of FAA compound or one salt thereof provided by said composition.

For animal supply, specifically a non-human mammalia, a food composition according to the present invention is suitable for a daily administration of active compound provided by said composition.

As used herein, a "food additive" useful according to the invention may be:
vitamins, such as vitamin A, vitamin D, vitamin E, vitamin K, vitamin C, folic acid, thiamine, riboflavin, vitamin B6, vitamin B12, niacin, biotin or pantothenic acid;
minerals such as sodium, potassium, phosphorus, magnesium, copper, zinc, iron, selenium, chromium and molybdenum;
soluble fibers such as agar-agar, alginate, locust bean, carrageenan, acacia gum, guar gum, karaya gum, pectin or xanthan gum, such soluble fibers being in hydrolyzed or non-hydrolyzed form;
energetic source compounds, especially one or more carbon hydrate source(s) selected from the group consisting of maltodextrins, starch, lactose, glucose, sucrose, fructose, xylitol and sorbitol and optionally fatty acids such as omega-3;
prebiotic, probiotic,
antioxidant,
flavonoids,
spices or aromatic herbs.

As used herein, a "food ingredient" useful according to the invention may be selected among fruit, vegetables, meat, fish, cereal, etc. or one of their combination.

The present invention also relates in one aspect to a food composition such as described above used under a form selected from: food supplement or dietary supplement for animal or human food, or ready-cooked dish, or animal feedstuff.

The present invention further relates to a cosmetic use of the oleic acid derivatives described above or of the food composition described above for improving the appearance of individuals, for example for slimming the figure and/or reducing or restraining localized fat accumulations or lipodystrophy, and/or for stimulating the loss of excess weight and/or of cellulite, and/or for limiting the accumulation thereof, in individuals who are in good health.

As used herein, treating "excess weight" is intended to mean that said cosmetic method is aimed at subjects (humans or animals, for example pets, farmed animals, sport-related animals or animals dedicated to shows) with a normal corpulence. In humans for example, people will be considered, who are in good health, the excess weight or fat accumulation of whom is not associated with pathological conditions or a growing burden of disease (typically glucose metabolism disorders, insulin resistance, metabolic syndrome, diabetes or vascular disorders) and the BMI of whom is from 18.5 to 25. In these subjects, excess weight or body fat typically exist as cellulite, is not associated with a growing burden of disease and is preferably distributed according to a gynoid pattern. A cosmetic treatment according to the present invention will therefore be especially suited to the treatment of cellulite, in particular on hips and buttock. It could be used for example in women who go through menopause or after pregnancy and, as a rule, in individuals having a sedentary lifestyle and/or a diet that is high in sugar or in fat, so as to contribute to preserve or to rediscover a slim body and to remove or prevent the development of cellulite. Such a treatment may also be useful in castrated animals so as to prevent the increase in body fat at the cost of muscular lean mass.

Weight loss is often induced through restrictive diets, that are hard to observe in the long term and that are frequently responsible for a so called rebound effect (or relapse) with, as a consequence, a new weight gain sometimes higher than the one induced through the caloric restriction itself. A cosmetic treatment method according to the present invention could thus be used as a complement to a restrictive diet while optionally increasing physical activity, so as to limit the intensity of the restriction, especially the caloric one, and so as to prevent any lean body mass loss and rebound effect when stopping the restrictive diet.

A cosmetic (i.e. non-therapeutic) use according to the present invention comprises the administration of the FAA compound according to the invention, preferably by oral administration.

Most preferably, the cosmetic use or food composition is adapted to oral administration and is intended to be taken as a food supplement such as previously described.

In other aspect, the present invention also relates to the cosmetic use of the oleic acid derivative described above or of the food composition described above:
as taste enhancer, as taste modulator, as appetite suppressant;
for improving the physical look of individuals, for example for body slimming and/or reducing or restraining localized fat accumulations or lipodystrophy, and/or for stimulating the loss of excess weight and/or of cellulite, and/or for limiting the accumulation thereof, in individuals who are in good health.

DESCRIPTION OF THE FIGURES

The present invention will be hereafter illustrated without being limited thereto by means of the following examples. It will be referred to the following figures in the examples:

FIG. 1B: Action of the CD36 inhibitor (20 µM SSO, Sulfo-N-succinimidyl Oleate) on the increase in intracellular free calcium concentrations, $[Ca^{2+}]I$ ($F_{340}/F_{380}$), by the oleic acid derivative described in FIG. 1A (compound 3a) in mouse taste bud cells loaded with Fura-2/AM probe—the arrow indicates the time when compound 3a, without any interruption in the recording, was added into the cuvette, containing the cells—the figure shows a single trace of several times reproduced experiments—the SSO completely blocked the responses triggered by OA and 3a;

FIG. 2B: Action of the CD36 inhibitor (20 μM SSO, Sulfo-N-succinimidyl Oleate) on the increase in intracellular free calcium concentration $[Ca^{2+}]I$ ($F_{340}/F_{380}$), by the oleic acid derivative described in FIG. 2A in mouse taste bud cells loaded with Fura-2/AM probe (the cells were pre-incubated for 15 minutes prior to the addition of 2a compound)—the arrow indicates the time when compound 2a, without any interruption in the recording, was added into the cuvette, containing the cells—the figure shows a single trace of several times reproduced experiments—the SSO partially blocked the responses triggered by OA and 2a;

EXAMPLES

Figure 1A:
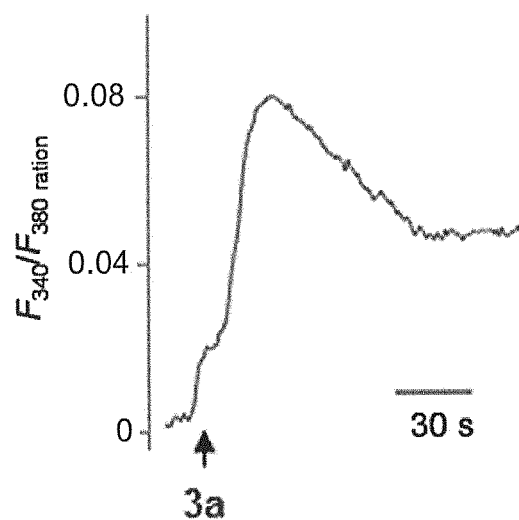
FIG. 1A: Measurement of intracellular free calcium concentrations, $[Ca^{2+}]i$ ($F_{340}/F_{380}$) induced by the introduction of one oleic acid derivative according to the invention: compound 3a, in mouse taste bud cells loaded with Fura-2/AM probe—the arrow indicates the time when compound 3a, without any interruption in the recording, was added into the cuvette, containing the cells—the figure shows a single trace of several times reproduced experiments.

1. Synthesis of Different Oleic Acid Derivatives of the Invention 1.1 Synthesis of (Z)-(3-methyloxetan-3-yl)methyl octadec-9-enoate, with n=1 and n'=1 and $R^4$=CH$_3$, Also Called, Compound 2a (17FM016)

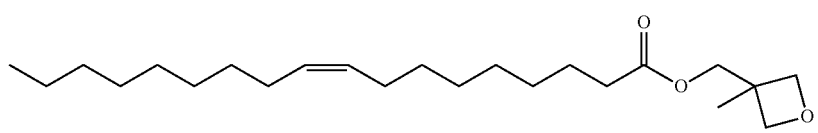 [SMILES: CCCCCCCC/C=C\CCCCCCCC(=O)OCC1COC1]

(Z)-3-methyloxetan-3-yl)methyl octadec-9-enoate
Chemical Formula: C$_{23}$H$_{42}$O$_3$
Molecular Weight: 366,59

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of 3-methyl-3-oxetane methanol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$. (petroleum ether/ethyl acetate (5:1), R$_f$=0.70). m$_{pure}$=231 mg. Aspect: colorless oil. Yield: 90%.

$^1$H NMR (500 MHz, CDCl$_3$) δ (ppm): 5.37-5.30 (m, 2H), 4.52 (d, 2H, J=6.0 Hz), 4.38 (d, 2H, J=6.0 Hz), 4.15 (s, 2H), 2.35 (t, 2H, J=7.6 Hz), 2.02-1.98 (m, 4H), 1.66-1.61 (m, 2H), 1.33-1.26 (m, 23H), 0.88 (t, 3H, J=7.0 Hz).

$^{13}$C {$^1$H} NMR (126 MHZ, CDCl$_3$) δ (ppm): 173.87, 129.99, 129.68, 79.56 (2×), 68.43, 39.06, 34.19, 31.87, 29.73, 29.65, 29.49, 29.28 (2×), 29.12, 29.09, 29.06, 27.18, 27.12, 24.94, 22.64, 21.17, 14.07.

IR (neat cm$^{-1}$) ν=3003 (small), 2923 (broad), 2854 (broad), 1739 (strong), 1460, 1377 (small), 1351 (small), 1239, 1162 (broad), 1119 (small), 1090 (small), 983 (strong), 940 (small), 834 (small), 722 (broad).

HRMS calcd for C$_{23}$H$_{43}$O$_3$ [M+H]$^+$=367.3207; found: 367.3207.

1.2 Synthesis of (E)-(3-methyloxetan-3-yl)methyl octadec-9-enoate, with n=1 and n'=1 and R$^4$=CH$_3$, Also Called, Compound 2b (17FM020)

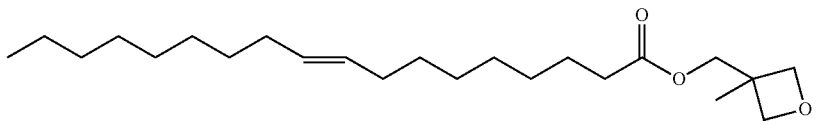

(E)-(3-methyloxetan-3-yl)methyl octadec-9-enoate
Chemical Formula: C$_{23}$H$_{42}$O$_3$
Molecular Weight: 366,59

In a round bottom flask were introduced elaidic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of 3-methyl-3-oxetane methanol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$. (petroleum ether/ethyl acetate (5:1), R$_f$=0.70). m$_{pure}$=212.7 mg. Aspect: white solid. Yield: 83%.

$^1$H NMR (500 MHZ, CDCl$_3$) δ (ppm): 5.43-5.32 (m, 2H), 4.52 (d, 2H, J=6.0 Hz), 4.38 (d, 2H, J=6.0 Hz), 4.16 (s, 2H), 2.35 (t, 2H, J=7.6 Hz), 1.98-1.94 (m, 4H), 1.70-1.56 (m, 3H), 1.37-1.22 (m, 22H), 0.88 (t, 3H, J=6.9 Hz).

$^{13}$C {$^1$H} NMR (126 MHZ, CDCl$_3$) δ (ppm): 173.89, 130.49, 130.18, 79.59 (2x), 68.45, 39.11, 34.22, 32.59, 32.53, 31.89, 29.65, 29.55, 29.48, 29.30, 29.17, 29.11, 29.09, 28.94, 24.98, 22.67, 21.20, 14.09.

IR (neat cm$^{-1}$) v=2963 (small), 2918 (strong), 2849 (strong), 1737 (strong), 1466, 1413, 1392, 1357 (small), 1314 (small), 1294 (small), 1253, 1209, 1162 (broad), 1095 (small), 1065 (small), 1041 (small), 999, 962 (strong), 932 (small), 908 (small), 836 (small), 776 (small), 757 (small), 720, 662 (small), 575 (small), 526 (small), 445 (small), 410 (small).

HRMS calcd for C$_{23}$H$_{43}$O$_3$ [M+H]$^+$: 367.3207; found: 367.3208.

1.3 Synthesis of (Z)-(tetrahydrofuran-2-yl)methyl octadec-9-enoate with n=3 and n'=0 and R$^4$=H, Called Hereafter Compound 2c (17FM060)

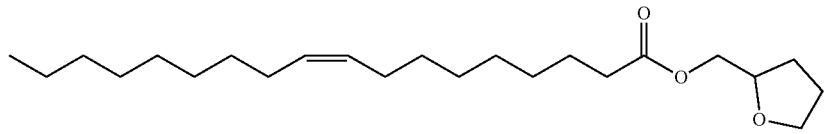 [SMILES: CCCCCCCC/C=C\CCCCCCCC(=O)OCC1CCCO1]

(Z)-(tetrahydrofuran-2-yl)methyl octadec-9-enoate
Chemical Formula: C$_{23}$H$_{42}$O$_3$
Molecular Weight: 366,59

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 µL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of (±)-tetrahydrofurfuryl alcohol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$ (petroleum ether/ethyl acetate (5:1), R$_f$=0.70). m$_{pure}$=235 mg. Aspect: colorless oil. Yield: 92%.

$^1$H NMR (500 MHZ, CDCl$_3$) δ (ppm): 5.41-5.26 (m, 2H), 4.16 (dd, 1H, J=3.6 Hz, J=11.2 Hz), 4.11 (qd, 1H, J=3.5 Hz, J=6.9 Hz), 3.99 (dd, 1H, J=6.6 Hz, J=11.3 Hz), 3.89 (dt, 1H, J=6.6 Hz, J=8.7 Hz), 3.83-3.76 (m, 1H), 2.34 (t, 2H, J=7.6 Hz), 2.00 (qd, 5H, J=2.2 Hz, J=6.3 Hz), 1.97-1.84 (m, 2H), 1.65-1.56 (m, 4H), 1.37-1.21 (m, 19H), 0.88 (t, 3H, J=6.8 Hz).

$^{13}$C {$^1$H} NMR (126 MHZ, CDCl$_3$) δ (ppm): 173.80, 129.98, 129.75, 76.56, 68.42, 66.31, 34.21, 31.89, 29.76, 29.68, 29.51, 29.31, 29.30, 29.15, 29.10, 29.09, 28.01, 27.21, 27.16, 25.65, 24.92, 22.66, 14.08.

IR (neat cm$^{-1}$) v: 3008 (small), 2924 (broad), 2854 (broad), 1737 (strong), 1458, 1362 (small), 1239, 1169 (broad), 1082 (broad), 1023, 991, 916, 722 (broad).

HRMS calcd for C$_{23}$H$_{43}$O$_3$ [M+H]$^+$: 367.3207; found: 367.3204.

1.4 Synthesis of (Z)-(tetrahydrofuran-3-yl) methyl octadec-9-enoate with n=2, n'=1 and R$^4$=H, Called Hereafter Compound 2d (18FM094)

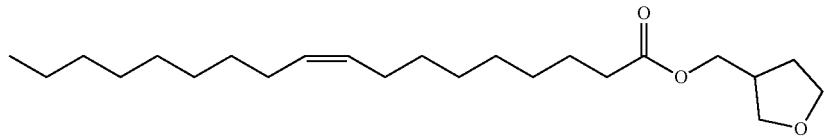 [SMILES: CCCCCCCC/C=C\CCCCCCCC(=O)OCC1CCOC1]

(Z)-(tetrahydrofuran-3-yl)methyl octadec-9-enoate
Chemical Formula: C$_{23}$H$_{42}$O$_3$
Molecular Weight: 366,59

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1h at 0° C. and for 2 h at room temperature. Solvents and oxalyl chloride were removed under reduced pressure and the product was directly engaged in the following step. Aspect: yellow oil with slight precipitate.

A solution of tetrahydro-3-furanmethanol (0.14 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$. (petroleum ether/ethyl acetate (5:1), R$_f$=0.70), m=236.1 mg. Aspect: colorless oil. yield: 93%.

$^1$H NMR (500 MHZ, CDCl$_3$) δ (ppm): 5.34 (qd, 2H, J=1.9 Hz, J=3.9 Hz), 4.09 (dd, 1H, J=6.5 Hz, J=10.9 Hz), 3.97 (dd, 1H, J=8.0 Hz, J=10.9 Hz), 3.90-3.82 (m, 2H), 3.79-3.71 (m, 1H), 3.56 (dd, 1H, J=5.6 Hz, J=8.8 Hz), 2.62-2.51 (m, 1H), 2.30 (t, 2H, J=7.5 Hz), 2.08-1.96 (m, 5H), 1.67-1.57 (m, 4H), 1.37-1.20 (m, 19H), 0.88 (t, 3H, J=6.9 Hz).

$^{13}$C {$^1$H} NMR (126 MHZ, CDCl$_3$) δ (ppm): 173.77, 130.00, 129.71, 70.54, 67.70, 65.66, 38.26, 34.25, 31.89, 29.75, 29.67, 29.50, 29.30 (2x), 29.14, 29.10, 29.08, 28.94, 27.20, 27.14, 24.95, 22.66, 14.09.

1.5 Synthesis of (Z)-(oxetan-3-yl)methyl octadec-9-enoate with n=1, n'=1 and R$^4$=H, Called Hereafter Compound 2e (17FM057)

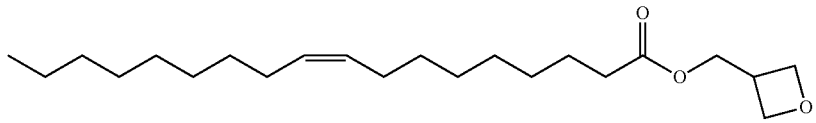

(Z)-(oxetan-3-yl)methyl octadec-9-enoate
Chemical Formula: C$_{22}$H$_{40}$O$_3$
Molecular Weight: 352,56

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1h at 0° C. and for 2 h at room temperature. Solvents and oxalyl chloride were removed under reduced pressure and the product was directly engaged in the following step. Aspect: yellow oil with slight precipitate.

A solution of 3-oxatane alcohol (0.12 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$. (petroleum ether/ethyl acetate (5:1), R$_f$=0.70). m$_{pure}$=233.5 mg. Aspect: colorless oil. Yield: 95%.

$^1$H NMR (500 MHZ, CDCl$_3$) δ (ppm): 5.40-5.29 (m, 2H), 4.79 (dd, 2H, J=6.3 Hz, J=7.9 Hz), 4.47 (t, 2H, J=6.2 Hz), 4.30 (d, 2H, J=6.7 Hz), 3.34-3.21 (m, 1H), 2.32 (t, 2H, J=7.6 Hz), 2.01 (q, 5H, J=6.3 Hz), 1.67-1.54 (m, 3H), 1.36-1.22 (m, 18H), 0.94-0.82 (m, 3H).

$^{13}$C {$^1$H} NMR (126 MHZ, CDCl$_3$) δ (ppm): 173.79, 130.01, 129.69, 74.09 (2x), 64.98, 34.16, 34.11, 31.88, 29.74, 29.66, 29.50, 29.29 (2x), 29.12, 29.08 (2x), 27.20, 27.14, 24.92, 22.65, 14.08.

IR (neat cm$^{-1}$) v=3003 (small), 2923 (broad), 2853 (broad), 1738 (strong), 1461, 1362 (small), 1240, 1164 (broad), 1119 (small), 1092 (small), 984 (strong), 946 (small) 855 (small), 723 (broad).

HRMS calcd for $C_{22}H_{41}O_3$ [M+H]$^+$: 353.3050; found: 353.3052.

1.6 Synthesis of (Z)-(oxiran-2-yl)methyl octadec-9-enoate with n=1, n'=0 and R$^4$=H, Called Hereafter Compound 2f (17FM066)

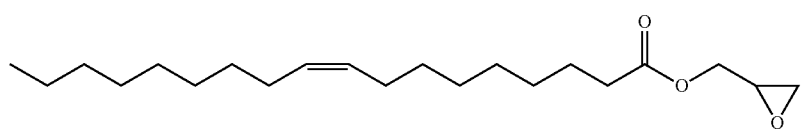

(Z)-(oxiran-2-yl)methyl octadec-9-enoate
Chemical Formula: $C_{21}H_{38}O_3$
Molecular Weight: 338,53

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1h at 0° C. and for 2 h at room temperature. Solvents and oxalyl chloride were removed under reduced pressure and the product was directly engaged in the following step. Aspect: yellow oil with slight precipitate.

A solution of glycidol (105.2 mg, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over MgSO$_4$ and purified by column chromatography on SiO$_2$. (petroleum ether/ethyl acetate (5:1), R$_f$=0.70). m$_{pure}$=235.5 mg. Aspect: colorless oil. Yield: 99%.

$^1$H NMR (500 MHz, CDCl$_3$) δ (ppm): 5.42-5.27 (m, 2H), 4.41 (dd, 1H, J=3.0 Hz, J=12.3 Hz), 3.91 (dd, 1H, J=6.3 Hz, J=12.3 Hz), 3.25-3.12 (m, 1H), 2.84 (td, 1H, J=1.5 Hz, J=4.4 Hz), 2.64 (dd, 1H, J=2.6 Hz, J=4.9 Hz), 2.38-2.28 (m, 2H), 2.07-1.92 (m, 4H), 1.63 (q, 2H, J=7.4 Hz), 1.36-1.27 (m, 20H), 0.88 (td, 3H, J=1.6 Hz, J=6.9 Hz).

$^{13}$C {$^1$H} NMR (126 MHZ, CDCl$_3$) δ (ppm): 173.52, 130.00, 130.72, 64.74, 49.38, 44.65, 34.13, 34.05, 31.89, 29.75, 29.67, 29.51, 29.31, 29.13, 29.08, 27.21, 27.15, 24.89, 24.85, 22.67, 14.09.

IR (neat cm$^{-1}$) v=3004 (small), 2923 (broad), 2853 (broad), 1739 (strong), 1458, 1374 (small), 1358 (small), 1243, 1172 (broad), 1118, 1092, 1052, 1017, 910 (small), 855 (small), 722 (small).

HRMS calcd for $C_{21}H_{38}O_3Na$ [M+Na]$^+$: 361.2713; found: 361.2714.

1.7 Synthesis of (Z)-oxopropyl octadec-9-enoate Called Hereafter Compound 2g (17FM064)

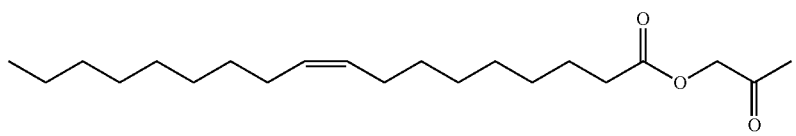 [SMILES: CCCCCCCC/C=C\CCCCCCCC(=O)OCC(C)=O]

(Z)-oxopropyl octadec-9-enoate
Chemical Formula: $C_{21}H_{38}O_3$
Molecular Weight: 338,53

In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1h at 0° C. and for 2 h at room temperature. Solvents and oxalyl chloride were removed under reduced pressure and the product was directly engaged in the following step. Aspect: yellow oil with slight precipitate.

A solution of hydoxyacetone (0.2 mL, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$. (petroleum ether/ethyl acetate (5:1.5), $R_f$=0.60). $m_{pure}$=234 mg. Aspect: colorless oil. Yield: 99%.

$^1$H NMR (500 MHZ, $CDCl_3$) δ (ppm): 5.43-5.25 (m, 2H), 4.64 (s, 2H), 2.42 (t, 2H, J=7.6 Hz), 2.16 (s, 3H), 2.08-1.94 (m, 4H), 1.67 (p, 2H, J=7.5 Hz), 1.34-1.26 (m, 20H), 0.88 (t, 3H, J=6.9 Hz).

$^{13}$C {1H} NMR (126 MHZ, $CDCl_3$) δ (ppm): 201.67, 173.02, 130.00, 129.74, 68.14, 33.81, 31.89, 29.76, 29.68, 29.51, 29.31, 29.30, 29.14, 29.08, 29.05, 27.21, 27.16, 26.05, 24.83, 22.67, 14.08

IR (neat $cm^{-1}$) v: 3004 (small), 2923 (broad), 2853, 1734 (strong), 1462 (broad), 1418 (broad), 1373 (broad), 1357 (broad), 1270 (small), 1239 (small), 1195 (small), 1153 (broad), 1120, 1094 (small), 1057 (small), 967 (small), 894 (small), 723 (broad).

HRMS calcd for $C_{21}H_{39}O_3$ $[M+H]^+$: 339.2894; found: 339.2893.

1.8 Synthesis of (Z)-(2,5,5-trimethyl-1,3-dioxan-2-yl)methyl octadec-9-enoate, Called Hereafter Compound 2h (17FM058)

This compound was prepared by reaction of oleic acid and 2,2,5-trimethyl-1,3-dioxane-5-methanol (called hereafter 17FM025), known in literature and prepared as describe below.

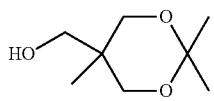

17FM025: In a round bottom flask were introduced tris(hydroxymethyl)ethane (2 g, 16.7 mmol) and a catalytic quantity of PTSA (2 mg) in acetone under inert atmosphere. The mixture was stirred at room temperature for 2 days. The reaction was neutralized with 50 mg of $K_2CO_3$, filtrated and evaporated to give the desired product with 96% of purity. $m_{pure}$=2.64 g. Aspect: colorless oil. Yield: 98%.

$^1$H NMR (500 MHZ, DMSO) δ (ppm): 4.57 (t, 1H, J=5.4 Hz), 3.49 (AB system, 2H, J=11.7 Hz), 3.44 (AB system, 2H, J=11.7 Hz), 3.35 (d, 1H, J=5.3 Hz), 1.33 (s, 3H), 1.27 (s, 3H), 0.75 (s, 3H).

$^{13}$C {1H} NMR (126 MHZ, DMSO) δ (ppm): 96.92, 65.34 (2x), 63.61, 34.22, 25.80, 21.57, 17.61.

Compound 2h: In a round bottom flask were introduced oleic acid (200 mg, 0.7 mmol) and dichloromethane (2 mL) under inert atmosphere. The mixture was cooled to 0° C. and oxalyl chloride (0.07 mL, 0.78 mmol) was introduced dropwise. Then the catalytic quantity of DMF (5 μL) was added. The reaction mixture was stirred for 1 h at 0° C. and for 2 h at room temperature. Solvents and oxalyl chloride were removed under reduced pressure and the product was directly engaged in the following step. Aspect: yellow oil with slight precipitate.

A solution of 2,5,5-trimethyl-1,3-dioxane-2-methanol (228 mg, 1.42 mmol), triethylamine (0.2 mL, 1.42 mmol) in THF (4 mL) was prepared in a round bottom flask under inert atmosphere. The mixture was cooled to 0° C. and freshly prepared oleoyl chloride (212 mg, 0.7 mmol) in THF (4 mL) was added via cannula. After stirring for overnight at RT, the mixture was worked up by addition of distilled water (6 mL). The product was extracted with ethyl acetate (3×15 mL), dried over $MgSO_4$ and purified by column chromatography on $SiO_2$. (petroleum ether/ethyl acetate (5:1), $R_f$=0.73). $m_{pure}$=262 mg. Aspect: colorless oil. Yield: 87%.

$^1$H NMR (500 MHZ, $CDCl_3$) δ (ppm): 5.47-5.18 (m, 2H), 4.15 (s, 2H), 3.70-3.57 (m, 4H), 2.32 (t, 2H, J=7.6 Hz), 2.14-1.88 (m, 4H), 1.63 (t, 2H, J=7.2 Hz), 1.44 (s, 3H), 1.40 (s, 3H), 1.37-1.19 (m, 20H), 0.88 (t, 3H, J=6.8 Hz), 0.85 (s, 3H).

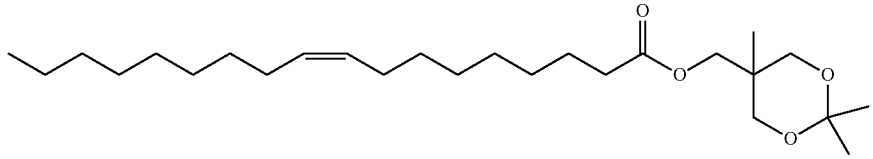 [SMILES: CCCCCCCC/C=C\CCCCCCCC(=O)OCC1(C)COC(C)(C)OC1]

Chemical formula: $C_{26}H_{48}O_4$
Molecular weight: 424.67

$^{13}$C {1H} NMR (126 MHZ, $CDCl_3$) δ (ppm): 173.77, 130.00, 129.73, 98.04, 66.63, 66.31 (2x), 34.30, 33.54, 31.89, 29.76, 29.68, 29.51, 29.31, 29.30, 29.15, 29.09, 27.21 (2x), 27.16, 26.74, 24.96, 22.67, 20.58, 17.80, 14.09.

IR (neat $cm^{-1}$) v=2993 (small), 2923 (broad), 2854 (broad), 1737 (strong), 1456 (broad), 1395 (small), 1372, 1349 (small), 1265 (broad), 1246 (broad), 1227 (broad), 1206 (broad), 1186 (broad), 1155 (broad), 1090 (strong), 1043, 1025 (broad), 933 (small), 912 (small), 830 (strong), 729 (broad), 673 (small).

HRMS calcd for $C_{26}H_{48}O_4Na$ $[M+Na]^+$: 447.3448; found: 447.3431.

1.9 Synthesis of ethyl (S)-[(Z)-heptadec-8-en-yl-4, 5-dihydrooxazole-4-carboxylate Called Hereafter Compound 2i (18FM100)

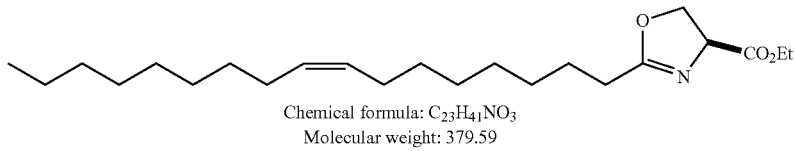 [SMILES: CCCCCCCC/C=C\CCCCCCCC1=N[C@H](C(=O)OCC)CO1]

Chemical formula: $C_{23}H_{41}NO_3$
Molecular weight: 379.59

In a round bottom flask were introduced (S)-ethyl-3-hydroxy-2((Z)-octadeca-9-enamido)-propanoate (500 mg, 1.26 mmol), dry DCM (3 mL) and $iPr_2NEt$ (0.5 mL, 2.77 mmol) under inert atmosphere. After 30 min, the mixture was cooled to 0° C. and Deoxofluor (0.6 mL, 2.77 mmol) was added dropwise. After 16h at room temperature, the crude mixture was directly engaged on $SiO_2$ gel chromatography for purification. (petroleum ether/ethyl acetate (6:4), $R_f$=0.71). $m_{pure}$=268.3 mg. Aspect: yellow oil. Yield: 56%.

$^1$H NMR (500 MHZ, $CDCl_3$) δ (ppm): 5.42-5.26 (m, 2H), 4.76-4.65 (m, 1H), 4.49-4.42 (m, 1H), 4.37 (dd, 1H, J=8.7 Hz, J=10.6 Hz), 4.30-4.17 (m, 2H), 2.38-2.27 (m, 2H), 2.08-1.94 (m, 4H), 1.70-1.59 (m, 3H), 1.38-1.21 (m, 22H), 0.88 (t, 3H, J=6.9 Hz).

$^{13}$C {$^1$H} NMR (126 MHZ, $CDCl_3$) δ (ppm): 171.38, 170.81, 129.97, 129.75, 69.26, 68.22, 61.57, 31.89, 29.75, 29.68, 29.50, 29.30, 29.09 (2x), 27.96, 27.20, 27.16, 25.91, 22.66, 14.13, 14.09. 2 C are missing.

HRMS calcd for $C_{23}H_{42}NO_3$ [M+H]$^+$: 380.3159; found: 380.3156.

1.10 Synthesis of ethyl (S)-3-hydroxy-2-[(Z)-octadec-9-enamido]propanoate Called Hereafter Compound 2j (18FM099)

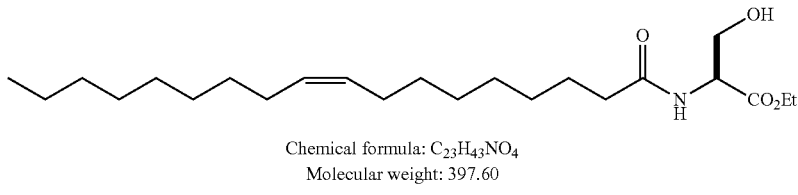 [SMILES: CCCCCCCC/C=C\CCCCCCCC(=O)N[C@@H](CO)C(=O)OCC]

Chemical formula: $C_{23}H_{43}NO_4$
Molecular weight: 397.60

This compound was prepared by reaction of oleic acid and L-serine ethyl ester hydrochloride salt (called hereafter 18FM097), known in literature and prepared as describe below.

18FM097

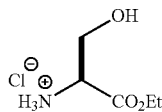

In a round bottom flask were introduced L-serine (2 g, 19.03 mmol) in ethanol (20 mL) under inert atmosphere. The mixture was cooled to 0° C. and $SOCl_2$ was added dropwise. The reaction mixture was refluxed overnight before evaporation to dryness to give the L-serine ethyl ester as hydrochloride salt. $m_{pure}$=2.5 g. Aspect: white solid. Yield: quant.

$^1$H NMR (500 MHz, DMSO) δ (ppm) δ 8.52 (s, 3H), 5.60 (t, 1H, J=5.1 Hz), 4.20 (q, 2H, J=7.1 Hz), 4.07 (t, 1H, J=3.6 Hz), 3.95-3.75 (m, 2H), 1.23 (t, 3H, J=7.1 Hz).

$^{13}$C {$^1$H} NMR (126 MHz, DMSO) δ (ppm): 168.42, 62.54, 59.85, 54.79, 14.36.

Compound 2j: In a round bottom flask were introduced oleic acid (1 g, 3.54 mmol), dry THF (50 mL), L-serine ethyl ester hydrochloride salt (600 mg, 3.54 mmol), (Benzotriazol-1-yloxy)tripyrrolidinophosphonium hexafluorophosphate (PyBOP) (2.03 g, 3.9 mmol) under inert atmosphere. The mixture was treated with $iPr_2NEt$ (1.36 mL, 7.8 mmol) and stirred for 4h at room temperature. After removing solvent under vacuum, the residue was dissolved in EtOAc, successively treated by HCl 1N, water, saturated aqueous $NaHCO_3$ and brine. The organic layer was dried over $MgSO_4$ and purified by column chromatography on $SiO_2$. (petroleum ether/ethyl acetate (1:3), $R_f$=0.58). $m_{pure}$=1.13 g. Aspect: white solid. Yield: 80%.

$^1$H NMR (500 MHZ, DMSO) δ (ppm): 8.01 (bd, 1H, J=7.6 Hz), 5.40-5.21 (m, 2H), 4.95 (t, 1H, J=5.7 Hz), 4.30 (dt, 1H, J=5.0 Hz, J=7.9 Hz), 4.07 (q, 2H, J=7.1 Hz), 3.63 (ddt, 2H, J=5.3 Hz, J=10.6 Hz, J=33.3 Hz), 2.17-2.08 (m, 2H), 2.06-1.91 (m, 4H), 1.56-1.44 (m, 2H), 1.30-1.12 (m, 23H), 0.85 (t, 3H, J=6.8 Hz).

$^{13}$C {$^1$H} NMR (126 MHZ, CDCl$_3$) δ (ppm): δ 173.80, 170.55, 129.87, 129.59, 63.27, 63.13, 61.70, 54.59, 36.34, 31.78, 29.65, 29.61, 29.40, 29.20 (2x), 29.17, 29.12, 29.04, 27.10, 27.07, 25.48, 22.56, 13.99.

HRMS calcd for C$_{23}$H$_{44}$NO$_4$ [M+H]$^+$: 398.3265; found: 398.3258.

1.11 Synthesis of diethyl (Z)-octadec-9-en-1-yl phosphonate, Called Hereafter Compound 3a (17FM026)

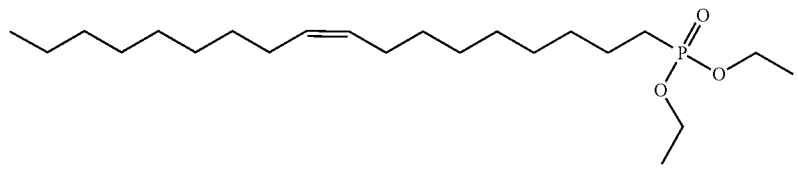

diethyl (Z)-octadec-9-en-1-yl phosphonate
Chemical Formula: C$_{22}$H$_{45}$O$_3$P
Molecular Weight: 388,57

This compound was prepared from oleic acid via the alcohol (17FM018) and the bromide (17FM023) described below. Both precursors are known in literature.

17FM018

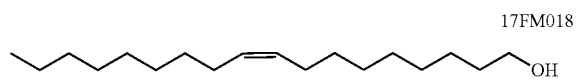 [SMILES: CCCCCCCC/C=C\CCCCCCCCO]

In a round bottom flask was suspended LiAlH$_4$ (0.36 g, 9.4 mmol) in THF (50 mL). A solution of oleic acid (2.5 mL, 7.9 mmol) in THF (20 mL) was added dropwise at 0° C. The mixture was slowly warmed up to room temperature and stirred overnight. The mixture was quenched by addition of distilled water (17 mL) and 15% aqueous NaOH (12 mL). The mixture was diluted in EtOAc, transferred in a separating funnel then washed with brine. The organic phase was dried over MgSO$_4$, filtered over celite and concentrated. The product was purified by a column chromatography on SiO$_2$. (petroleum ether/ethyl acetate (5:1), R$_f$=0.80). m$_{pure}$=1.9 g. Aspect: colorless oil. Yield: 75%.

$^1$H NMR (500 MHZ, CDCl$_3$) δ (ppm): 5.38-5.31 (m, 2H), 3.64 (t, 2H, J=6.7 Hz), 2.02-1.99 (m, 4H), 1.56 (quint, 2H, J=6.9 Hz), 1.36-1.27 (m, 22H), 0.88 (t, 3H, J=6.9 Hz).

$^{13}$C {$^1$H} NMR (126 MHZ, CDCl$_3$) δ (ppm): 129.93, 129.78, 63.06, 32.76, 31.87, 29.73, 29.71, 29.49, 29.47, 29.37, 29.29 (2x), 29.20, 27.18, 27.16, 25.71, 22.65, 14.07.

17FM023

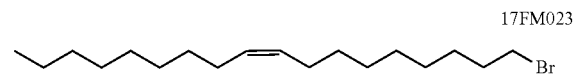 [SMILES: CCCCCCCC/C=C\CCCCCCCCBr]

In a round bottom flask containing (Z)-octadeca-9-en-1-ol (1.55 g, 5.8 mmol) in DCM (30 mL), was added carbon tetrabromide (3.5 g, 10.6 mmol) at 0° C., the mixture is let stirred for 10 minutes, then triphenylphosphine (3.1 g, 11.6 mmol) was added. The solution was stirred for 10 min at 0° C., then let warmed up overnight and concentrated under reduced pressure. The product was purified by a column chromatography on SiO$_2$. (petroleum ether, R$_f$=0.90). m$_{pure}$=1.9 g. Aspect: colorless oil. Yield: 99%.

$^1$H NMR (500 MHZ, CDCl$_3$) δ (ppm): 5.36-5.29 (m, 2H), 3.38 (t, 2H, J=6.9 Hz), 2.01-1.97 (m, 4H), 1.83 (quint, 2H, J=7.2 Hz), 1.43-1.37 (m, 2H), 1.39-1.31 (m, 20H), 0.86 (t, 3H, J=7.1 Hz)

$^{13}$C {$^1$H} NMR (126 MHZ, CDCl$_3$) δ (ppm): 130.01, 129.76, 33.94, 32.84, 31.90, 29.76, 29.70, 29.52, 29.32 (2x), 29.16, 28.74, 28.17, 27.21, 27.16, 22.67, 14.08, one C is missing.

Compound 3a (17FM026)

In a Schlenk were introduced diethyl phosphite (1.3 mL, 10.3 mmol) and THF (8 mL). The mixture was cooled to 0° C. and NaHMDS 2M (6.0 mL, 12.0 mmol) was added. The mixture was stirred at room temperature for half an hour. Then the reaction was cooled to 0° C. and (Z)-octadec-9-en-1-yl-bromide (1.4 g, 4.3 mmol) in THF (8 mL) was transferred on the reaction mixture via canula. After 30 minutes, the mixture was stirred overnight at 25° C. The reaction medium was concentrated under reduced pressure, and purified by column chromatography on SiO$_2$. (petroleum ether/ethyl acetate (1:4), R$_f$=0.50). m$_{pure}$=1.34 g. Aspect: slightly yellow oil. Yield: 80%.

$^1$H NMR (500 MHZ, CD$_2$Cl$_2$) δ (ppm): 5.37-5.31 (m, 2H), 4.14-4.03 (m, 4H), 2.04-1.98 (m, 4H), 1.75-1.54 (m, 5H), 1.62-1.57 (m, 2H), 1.38-1.24 (m, 25H), 0.88 (t, 3H, J=7.0 Hz)

$^{13}$C {$^1$H} NMR (126 MHZ, CD$_2$Cl$_2$) δ (ppm): 129.98, 129.78, 67.09, 61.38 (d, J=7.2 Hz), 53.42, 31.90, 30.69, 30.55, 29.76, 29.73, 29.52, 29.32, 29.31 (d, J=2.9 Hz), 29.23, 29.08, 27.20 (d, J=3.0 Hz), 26.26, 25.14, 22.68, 22.40 (d, J=5.0 Hz), 16.47 (d, J=6.7 Hz), 14.11

$^{31}P\{^1H\}$ NMR (203 MHZ, CDCl$_3$) δ (ppm): +32.65.

IR (neat cm$^{-1}$) v=2922 (broad), 2853, 1462 (small), 1391 (small), 1368 (small), 1243 (broad), 1163 (small), 1096 (small), 1056 (broad), 1028 (strong), 955 (broad), 813 (small), 784 (small), 722 (small).

HRMS calcd for C$_{22}$H$_{45}$O$_3$PNa [M+Na]$^+$: 411.2999; found 411.2998.

1.11 Synthesis of dibutyl (Z)-octadec-9-en-1-yl phosphonate, Called Hereafter Compound 3c (18FM110)

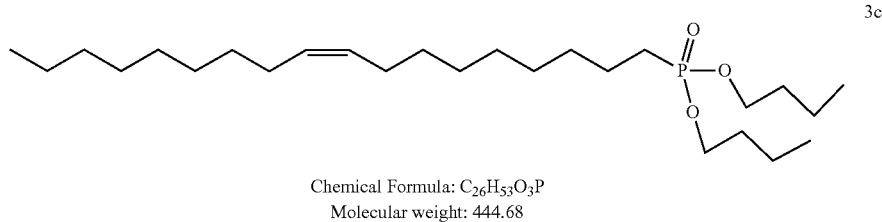 [SMILES: CCCCCCCC/C=C\CCCCCCCCP(=O)(OCCCC)OCCCC]

Chemical Formula: C$_{26}$H$_{53}$O$_3$P
Molecular weight: 444.68

This compound was prepared from oleic acid via the alcohol (17FM018) and the bromide (17FM023) described above. Both precursors are known in literature.

In a Schlenk were introduced dibutyl phosphite (0.74 mL, 3.79 mmol) and THF (4 mL). The mixture was cooled to 0° C. and NaHMDS 2M (2.12 mL, 4.24 mmol) was added. The mixture was stirred at room temperature for half an hour. Then the reaction was cooled to 0° C. and (Z)-octadec-9-en-1-yl-bromide (500 mg, 1.51 mmol) in THF (4 mL) was transferred on the reaction mixture via canula. After 30 minutes, the mixture was stirred overnight at 25° C. The reaction medium was concentrated under reduced pressure, and purified by column chromatography on SiO$_2$. (petroleum ether/ethyl acetate (1:1), R$_f$=0.50). m$_{pure}$=537.4 mg. Aspect: slightly yellow oil. Yield: 80%.

$^1$H NMR (500 MHZ, CDCl$_3$) δ (ppm): 5.37-5.31 (m, 2H), 4.01 (qq, 4H, J=6.7 Hz, J=10.0 Hz), 2.02-1.99 (m, 4H), 1.74-1.54 (m, 8H), 1.44-1.26 (m, 32H), 0.93 (t, 6H, J=7.4 Hz), 0.88 (t, 3H, J=6.9 Hz).

$^{13}$C $\{^1H\}$ NMR (126 MHZ, CDCl$_3$) δ (ppm): 129.96, 129.77, 65.16, 65.10, 32.64, 32.59, 31.89, 30.67, 30.53, 29.75, 29.72, 29.50, 29.30, 29.28, 29.22, 29.07, 27.20, 27.18, 26.09, 24.97, 22.67, 22.45, 22.40, 18.76, 14.09, 13.62

$^{31}$P $\{^1H\}$ NMR (203 MHZ, CDCl$_3$) δ (ppm): +32.58.

HRMS calcd for C$_{26}$H$_{53}$O$_3$PNa [M+Na]$^+$: 467.3617; found: 467.3625.

2. Biological Properties

2.1 Materials and Methods a—Animals

Eight weeks old, male mice (C$_{57}$BI/6 black) were purchased from the Janvier Elevage (Le Mans) and used for the experiments.

b—Isolation of Taste Bud Cells

The experimental protocol for isolation/purification of taste cells from fungiform papillae was approved by the Regional Ethical Committee (protocol number: A$^{0508}$).

The technique to isolate taste bud cells from mouse fungiform papillae has been described in the publication of El-Yassimi A, Hichami A, Besnard P, Khan N A. "Linoleic acid" induces calcium signaling, Src kinase phosphorylation, and neurotransmitter release in mouse CD36-positive gustatory cells"—*J. Biol. Chem.* 2008 May 9, 283(19), 12949-59.

Briefly, lingual epithelium was separated by enzymatic dissociation which contained the following: elastase and dispase mixture, 2 mg/ml each, in Tyrode's buffer (120 mM NaCl; 5 mM KCl; 10 mM HEPES ((4-(2-hydroxyethyl)-1-piperazineethanesulfonic acid); 1 mM CaCl$_2$); 1 mM MgCl$_2$; 10 mM glucose; 10 mM Na pyruvate, pH 7.4). The taste bud cells were isolated by incubating lingual epithelium in RPMI 1640 medium containing 2 mM EDTA, 1.2 mg/ml elastase, 0.6 mg/ml collagenase (type I), and 0.6 mg/ml trypsin inhibitor at 37° C. for 10 minutes, followed by centrifugation (600 g, 10 minutes). The cell populations, after separation, were suspended in fresh RPMI 1640 medium containing 10% fetal calf serum, 200 U/ml penicillin, and 0.2 mg/ml streptomycin, seeded onto a Poly-D-Lysine-coated dishes, and cultured for 24 hours. At the end of this period, the cells were used for the experiments or stained with trypan blue to assess their viability.

c—"Ca$^{2+}$ Signaling" for Showing the Interaction with CD36 and/or GPR120 Fat Taste Receptors Ca$^{2+}$ is the key second messenger in mammalian cells. It regulates a variety of cellular functions. Phospholipase C (PLC) is responsible for the hydrolysis of phosphatidylinositol-4,5-bisphosphate (PIP$_2$), generating two second messengers, i.e., inositol-1,4,5-triphosphate (hereafter IP$_3$) and diacylglycerol (DAG). The PLCβ subfamily is of particular interest, given its prominent role in neuronal and Taste Bud Cells (TBC) signaling, and its regulation by G Protein-Coupled Receptors (hereafter GPCR). IP$_3$ is freely diffusible and binds to IP 3-specific receptors, leading to the release of Ca$^{2+}$ from the endoplasmic reticulum (ER) which represents the intracellular Ca$^{2+}$ pool.

As regards taste perception, an increase in [Ca$^{2+}$]i has been considered as one of the earliest mechanisms, involved in the transfer of taste message from the tongue to the brain. The publication of El-Yassimi et al. (2008) mentioned above shows that CD36 and GPR120 (Ozdener M. H. et al. "CD36- and GPR120-mediated Ca$^{2+}$ signaling in human taste bud cells mediates differential responses to fatty acids and is altered in obese mice"—*Gastroenterology* 2014 April, 146 (4), 995-1005) in human and mouse taste bud cells are coupled to an increase in free $[Ca^{2+}]i$ during their activation by fatty acids like linoleic acid. Oleic acid also triggered the same response (unpublished observations). In mouse taste bud cells, the fatty acids via CD36 induced the phosphorylation of src-kinases, (Fyn[59] and Yes[62]) and regulated the increases in $[Ca^{2+}]i$ by opening of $Ca^{2+}$ channels (El-Yassimi et al. 2008), whose opening was controlled by stromal interaction molecule-1, STIM-1 (publication Dramane G. et al. "STIM1 regulates calcium signaling in taste bud cells and preference for fat in mice", *J. Clin. Invest.* 2012 June, 122(6), 2267-82).

Thus, it can be stated that $Ca^{2+}$ signaling (under the control of STIM1), plays a key role in the signaling of fat taste transduction in mice.

Therefore, the mobilization of intracellular $Ca^{2+}$ in response to the fatty acid derivatives of the invention was studied by the Applicant.

d—Method of Measurement of the $Ca^{2+}$ Signaling in Mouse Bud Cells

The mouse taste bud cells were seeded in 24-well plates (with glass bottom), containing poly-D-lysine for better adhesion to the surface. After 24 h, taste cells were incubated for 45 minutes with a fluorescent probe, Fura-2/AM (1 μM) in calcium buffer (110 mM NaCl, 5.4 mM, KCl, 25 mM, NaHCO$_3$, 0.8 mM, MgCl$_2$, 0.4 mM, KH$_2$PO$_4$, 20 mM, Hepes-Na, 0.33 mM, NaHPO$_4$, 1.2 mM, CaCl$_2$), pH 7.4). Then, the cells are washed with phosphate buffer saline (PBS) and taken up in calcium buffer.

The changes in intracellular $Ca^{2+}$ ($F_{340}/F_{380}$) were monitored under a Nikon microscope (TiU) by using an S Fluor 40× oil immersion objective.

Especially, the increases in $[Ca^{2+}]i$ were measured as follows: the mice taste bud cells were cultured on Willico-Dish wells with a glass bottom and loaded with a fluorescent probe, Fura-2/AM. The changes in intracellular $Ca^{2+}$ ($F_{340}/F_{380}$) were monitored under the Nikon microscope (TiU) by using S-fluor 40× oil immersion objective. The planes were taken at Z intervals of 0.3 μm, and NIS-Elements software was used to deconvolve the images. The microscope was equipped with EM-CCD (Lucas) camera for real time recording of 16-bit digital images. The dual excitation fluorescence imaging system was used for studies of individual cells. The changes in intracellular $Ca^{2+}$ were expressed as ΔRatio, which was calculated as the difference between the peak $F_{340}/F_{380}$ ratio. The data were summarized from the large number of individual cells (20-40 cells in a single run, with 3-9 identical experiments done in at least three cell preparations). The results were analyzed with the NIS-elements software, the variation in $[Ca^{2+}]i$ is expressed as A ratio ($F_{340}/F_{380}$) which was calculated with the difference of spectra at two wavelengths, i.e., 340 nm and 380 nm.

CD36: in order to assess if the oleic acid derivatives according to the invention exert their actions via CD36, the sulfo-N-succinimidyl oleate (SSO) was used. SSO is a CD36 inhibitor/blocker/antagonist.

Experiments were performed in the presence or absence of SSO with respect to calcium signaling to verify whether our analogs act well via this lipid receptor. Especially, for this assay with compounds 3a, 2a and oleic acid (control) were tested.

GPR120: in order to assess if the oleic acid derivatives according to the invention exert their actions via GPR120, AH7614 was used. This commercially available compound is a GPR120 antagonist.

Experiments were performed in the presence or absence of SSO or AH7614 with respect to calcium signaling to verify whether our analogs exert their action via this lipid receptor. Especially, for this assay compounds 3a, 2a and oleic acid (control) were tested.

2.1 Results a—Action on CD36 Fat Taste Receptor (FIG. 1 and FIG. 2)

Figure 1B:
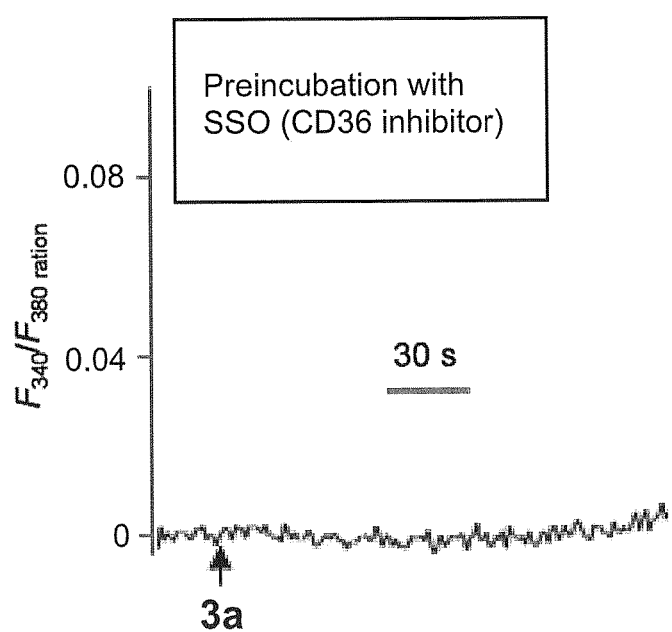

FIG. 1A shows that compound 3a, in mice taste bud cells, induces a huge increase in $[Ca^{2+}]i$ via CD36. This phenomenon is, however, abolished by the presence of SSO as it is shown in FIG. 1B. This figure proves that compound 3a is a complete CD36 agonist (i.e. binds to CD36) as its action was completely suppressed by SSO.

Figure 2A:
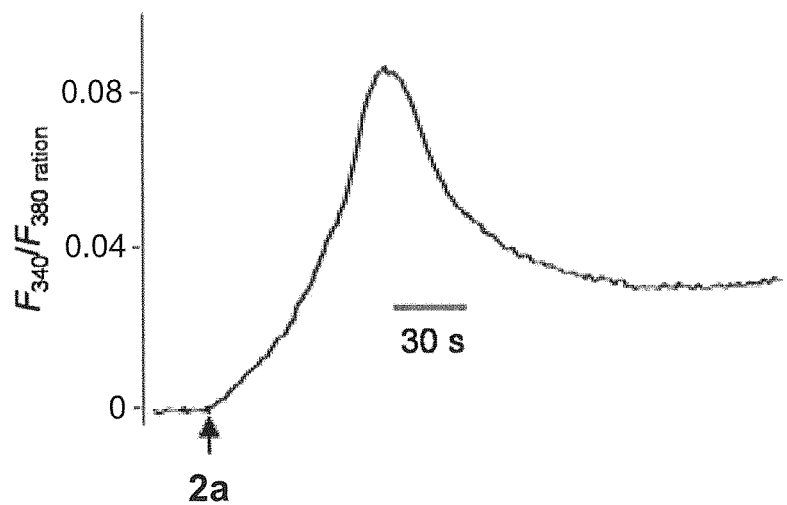
FIG. 2A: Measurement of intracellular free calcium concentrations, $[Ca^{2+}]i$ ($F_{340}/F_{380}$) induced by the introduction of one oleic acid derivative according to the invention: compound 2a, in mouse taste bud cells loaded with Fura-2/AM probe—the arrow indicates the time when the agonist (2a), without any interruption in the recording, was added into the cuvette, containing the cells—the figure shows a single trace of several times reproduced experiments.
Figure 2B:
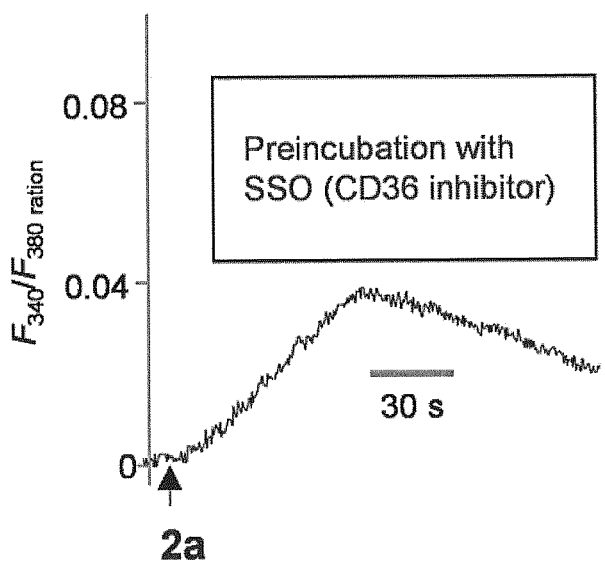

FIG. 2A also shows that compound 2a, in mice taste bud cells, induces a huge increase in $[Ca^{2+}]i$ via CD36. The compound 2a appears to be a partial agonist because its action on the increases in $[Ca^{2+}]i$ was curtailed, but not completely suppressed, by SSO (FIG. 2B). b-action on GPR120 fat taste receptor (FIG. 3)

Figure 3:
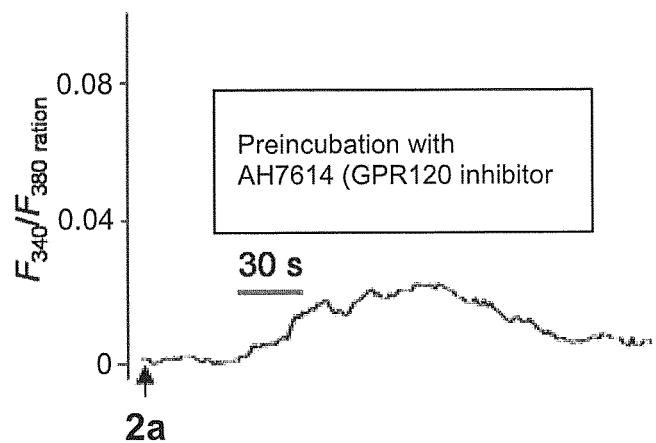
FIG. 3: Effect of GPR120 inhibitor (AH7614 that is a commercially available known GPR120 antagonist) at 20 μM on the increase in $[Ca^{2+}]I$ ($F_{340}/F_{380}$) by the oleic acid derivative 2a according to the invention (at 50 μM) in mouse taste bud cells, the cells were pre-incubated for 15 minutes prior to the addition of 2a compound—the arrow indicates the time when the agonist (2a), without any interruption in the recording, was added into the cuvette, containing the cells—the figure shows a single trace of several times reproduced experiments.

As it is shown by FIG. 3, compound 2a according to the invention also acts via GPR120 since AH7614 abolished, at least partially, its action on the increase in $[Ca^{2+}]i$ in mouse gustatory cells. Indeed, FIG. 3 shows that the response of compound 2a was significantly curtailed, but not suppressed, by AH7614.

Thus, these results show that compound 2a acts on both receptors CD36 and GPR120.

3. Fat-Like Taste Perception 3.1 Materials and Methods a—Animals

Eight weeks old, male mice (C57BI/6 black) were purchased from the "Janvier Elevage" (Le Mans) and used for these experiments.

b—Methods of Two-Bottle Preference Test

The mice are placed individually in cages in a controlled environment (humidity and constant temperature) and have free access to a standard diet. 6 hours before the tests, the mice are deprived of water.

During the behavioral experiments, the mice were offered two bottles simultaneously for 12 hours (night period).

The mice are subjected to a choice between the "control" solution and the experimental solution (FIG. 4 and FIG. 5).
  control solutions contain 0.3% xanthan gum, w/v, (Sigma Life Science, USA) in water to reproduce lipid texture and minimize bias due to differences in appearance between the two bottles;
  the experimental solution contains, either the "test compound" according to the invention at a concentration varying from 10 to 100 μM (compound 3a, FIG. 4 or compound 2a, FIG. 5) or only xanthan gum at 0.2% (v/v) (control test). To avoid the preference for one side, the position of each bottle is changed during each test.

To estimate the consumption of control and experimental solutions, the bottles are weighed before and after each experiment. The mice are allowed to take rest for 48 hours between each experiment.

Figure 4:
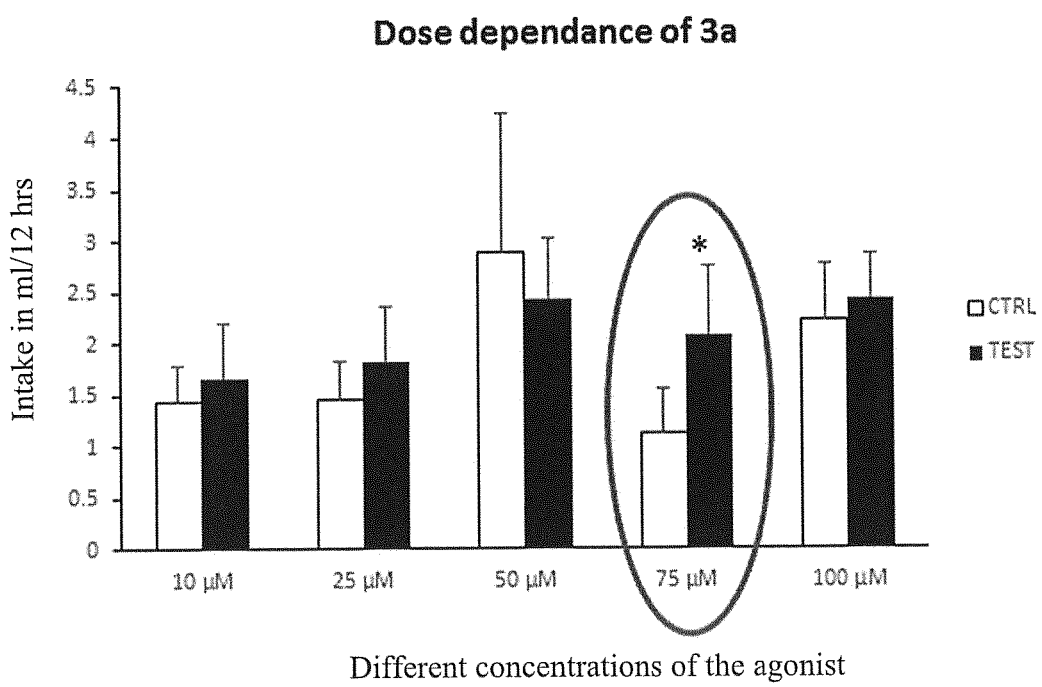
FIG. 4: Gustatory preference for the oleic acid derivative 3a according to the invention in a two bottle-preference test; this figure shows the dose-dependent effect of 3a; n=18 per group; the asterisk shows the significant difference as compared to the control solution (p<*) as per statistical students t-test of significance: the mice are subjected to two bottles: one (CTRL=control) containing water plus xanthan gum) and other TEST contains the same mixture and compound 3a at increasing concentrations as mentioned in the Figure—the bottles were weighed before and after 12 hrs of interval and the solution consumed by the animals was deduced.
Figure 5:
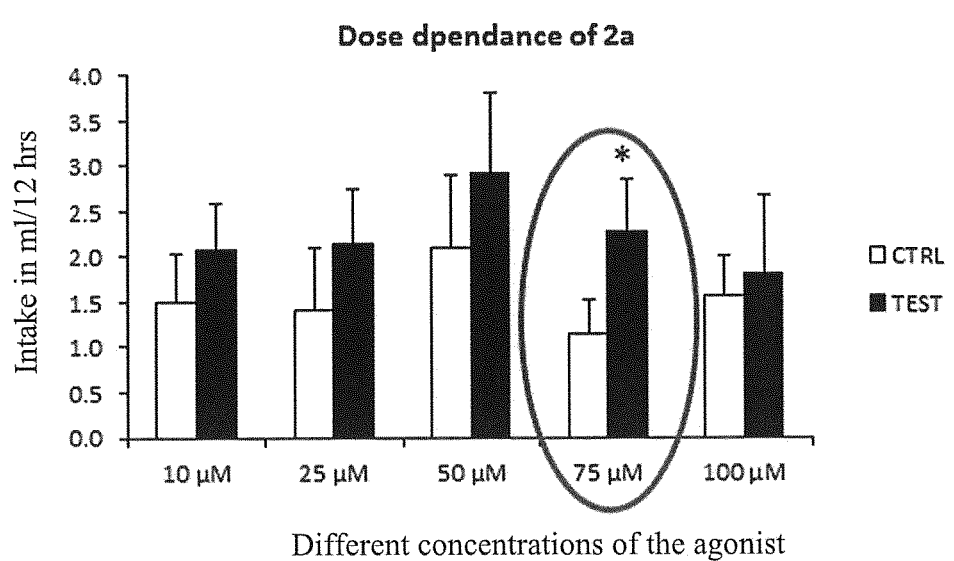
FIG. 5: Gustatory preference for the oleic acid derivative 2a according to the invention in a two bottle-preference test; this figure shows the dose-dependent effect of 2a; n=18 per group; the asterisk shows the significant difference as compared to the control solution (p<*) as per statistical students t-test of significance: the mice are subjected to two bottles: one (CTRL=control) containing water plus xanthan gum) and other TEST contains the same mixture and compound 2a at increasing concentrations as mentioned in the Figure—the bottles were weighed before and after 12 hrs of interval and the solution consumed by the animals was deduced.

3.2 Results (FIG. 4 to FIG. 5)

a—Compound 3a

As it is shown by FIG. 4, mice exhibit spontaneous preference for a solution containing the oleic acid derivative according to the invention, i.e. compound 3a as compared to the control (CTRL) solution containing xanthan gum. The preference is optimal at a concentration of 75 μM of compound 3a.

b—Compound 2a

Similarly, mice exhibit spontaneous preference for a solution containing compound 2a. It can be observed from FIG.

5 that mice prefer compound 2a at 75 μM. This is much lesser (102 times) than the concentration that is used for oleic acid in two-bottle preference tests.

4. Anti-Obesity Effects 4.1 Materials and Methods
a—Mice and Diet-Induced Obesity:

C57BL/6J male mice, aged between 6 to 10 weeks (16-20 g), were obtained from Janvier Labs (France). They were housed individually in a controlled environment with a 12 h light/dark cycle with food (SAFE, France) and water ad libitum. The palm oil (Huilerie Vigean, France) was the main fat component in high-fat diets. The high-fat diet was prepared weekly and stored at 4° C. until further use. The study was conducted as per Declaration of Helsinki and European ethical guidelines for the care and use of animals for experimentation. All the experimental protocols (protocol number: 16158) were approved by the Regional Ethical Committee of the University of Burgundy (Dijon, France).

The mice were grouped at random (n=10/group) and fed with either of the following diets: standard diet (STD) or high-fat diet (HFD). The body weight, food, and water intake were measured, weekly.

| Composition of the diets | | |
|---|---|---|
| Content (%) | STD | HFD |
| Proteins | 66.8 | 40.07 |
| starch | 16.10 | 14.6 |
| Fats | 3.10 | 35.3 |
| Cholesterol | — | 0.03 |
| Cellulose | 3.9 | 2.7 |
| Vitamins | 5 | 3.4 |
| Minerals | 5.1 | 3.9 |
| Energy (Kcal/100 g) | 359.5 | 536.65 |
| Fat energy (% of total energy) | 8 | 60 |

| Fatty acid composition of the diets | | |
|---|---|---|
| Fatty acids (%) | STD | HFD |
| SFA | 18.82 | 45.85 |
| MUFA | 26.38 | 40.02 |
| PUFA | 54.8 | 14.13 |

Standard diet (STD);
high-fat diet (HFD)
SFA: saturated fatty acids;
MUFA: monounsaturated fatty acids;
PUFA: polyunsaturated fatty acids.

After 10 weeks of feeding the diets, obese animals were divided into two groups: one groups continued to be fed on the same HFD; however, another group was fed on the same diet and received either NKS-3 or NKS-5) until $28^{th}$ of weeks of experimentation. At the end, the animals were sacrificed, under a fasting condition, and used for different analysis in blood and different tissues.

b—Determination of the Inflammatory Marker:

The CRP concentration was determined in sera by an automatic analyzer (Gilford Model 2000 system, a Beckman System T.R).

c—Statistical Analysis:

Results are expressed as mean±SEM (standard error of mean). Data were analyzed by using Statistica (4.1, Statsoft, Paris, France). The significance of difference between groups was determined by one-way analysis of variance (ANOVA), followed by least-significant-difference (LSD) test. For all the tests, the significance level chosen was p<0.05.

Figure 6A:
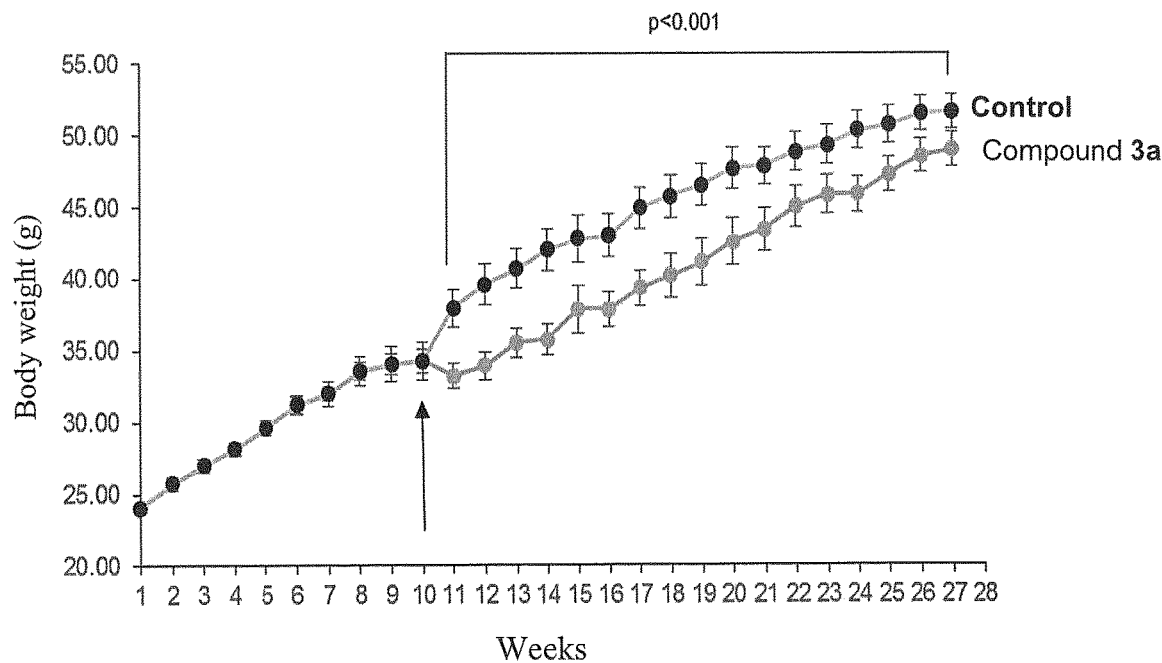
FIG. 6: Effect of oleic acid derivative 3a (FIG. 6A) and oleic acid derivative 2a (FIG. 6B) on diet-induced obesity. The animals were kept on a high-fat diet (HFD) for 28 weeks; however, from $10^{th}$ week onwards, the baby-bottles/feeders contained either control solution (control group) or analogues (3a or 2a). The arrows indicate when the lipid analogues were added. The results are expressed as the means±SEM (n=10). p values represent the significant differences between the group of mice given either water and analogues in the feeder bottles.
Figure 6B:
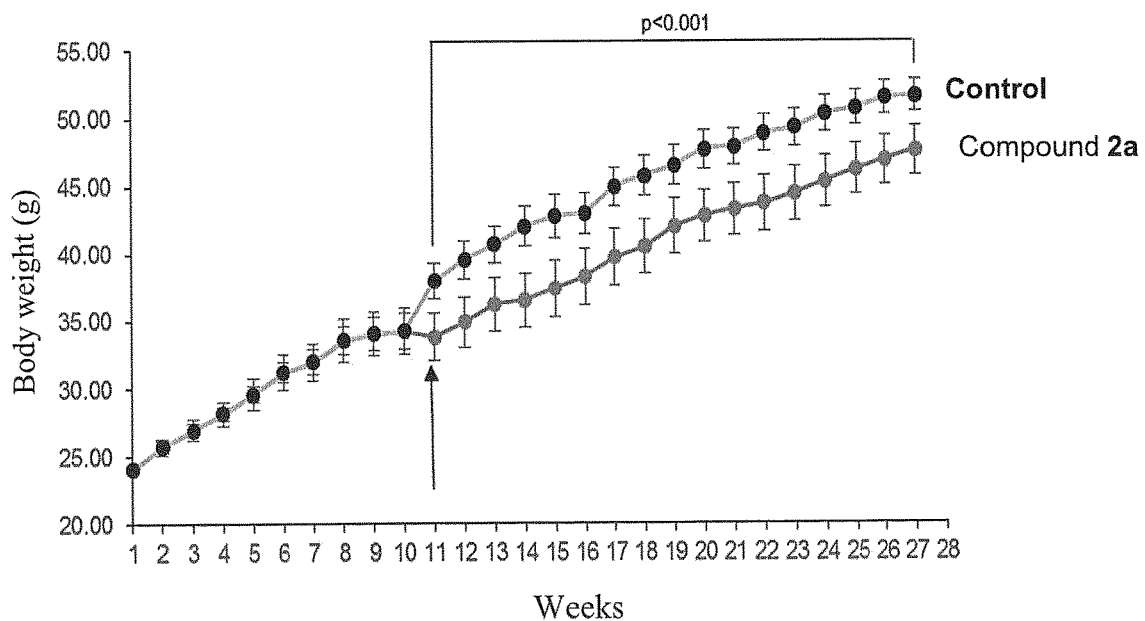

4.2 Fat Taste Analogues Exert Anti-Obesity Effects in Mice:

In order to elucidate the beneficial effects and especially during obesity, experiments were conducted on obese C57BL/6J mice. The mice were maintained on a high-fat diet for 10 weeks and an increase in body weight in a progressive and linear manner was observed in these animals. In order to test the curative/interventional effects on obesity, the animals were divided into two groups: one group that consumed only the high-fat diet (HFD) and the other consuming the same diet and also receiving 3a or 2a in ad libitum baby bottles/feeders. From the 10th week of the diet, we introduced lipid analogues into the bottles at 75 μM that corresponded to their preference in the double choice test. From the first week of administration of analogues, there was a significant decrease in body weight in the obese mouse by these two lipid analogues (2a was more powerful than 3a). In addition, the decrease in obesity was maintained until the 28th week of feeding a HFD (FIGS. 6A and 6B). The study was stopped after the 28th week of the diet because the animals reached the age of 34 weeks and beyond that age, the aging factor may interfere with the growth.

Figure 7:
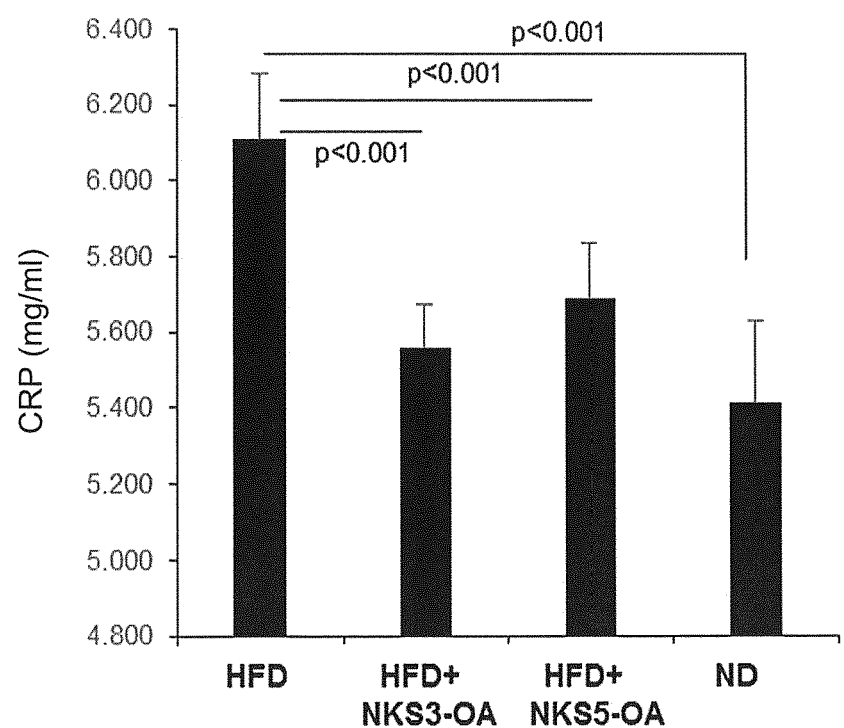
FIG. 7: CRP concentrations in blood circulation. The results are expressed as the means±SEM (n=10). p values represent the significant differences between the group of mice given either water and analogues in the feeder bottles. Abbreviations: HFD=high-fat diet.

4.3 Fat Taste Analogues Decrease Inflammatory Marker in the Blood in Mice:

The C-reactive protein (CRP), synthesized in the liver, is a protein that appears in the blood during inflammatory conditions such as obesity. It rises rapidly after the onset of inflammation. It is, therefore, a stable biological marker for detecting inflammation at an early stage. The CRP appears in all inflammatory processes and does not cross the placenta. FIG. 7 shows that the two oleic acid analogues (3a and 2a) significantly decreased the concentrations of circulating CRP, demonstrating that these agents also normalize the inflammatory status in obese mice.

The invention claimed is:

1. An oleic acid derivative of Formula (Z)-(I) or (E)-(I):

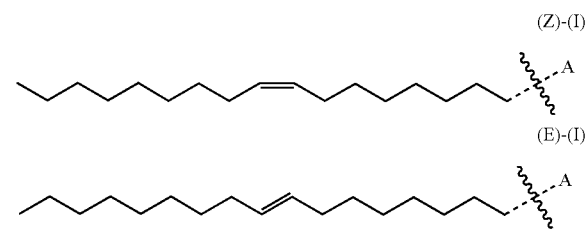

wherein group A is selected from $A^1$ to $A^3$ below:

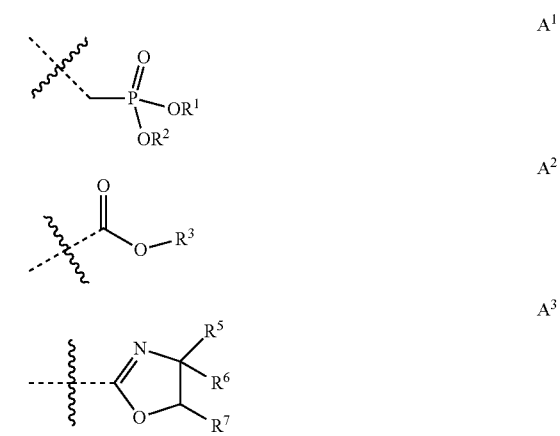

wherein $R^1$ and $R^2$ are each independently selected from the group consisting of ·H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is —$CH_2$—$CH_2$— or —$(CH_2)_3$—;

with the proviso that:

when $R^1$ or $R^2$=H, respectively $R^2$ or $R^1$ is different from H and from a straight alkyl group containing 2 or 8 carbon atoms, and when $R^1$ or $R^2$=—$CH_2CH_3$ or —$CH(CH_3)_2$ or —$(CH_2)_3CH_3$, $R^1$ and $R^2$ are not identical;

$R^3$ is independently selected from the group consisting of

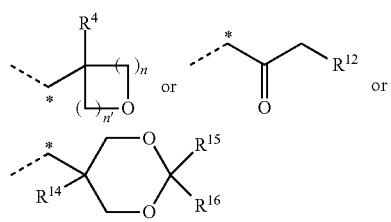

wherein $R^4$ is independently selected from the group consisting of a saturated or unsaturated, straight or branched alkyl group containing 1 to 4 carbon atoms, n is an integer selected from 1 to 4, and n' is an integer that is equal to 0 or 1; "*" is the carbon atom which is attached to the oxygen atom of the $A^2$ group;

$R^{12}$ is independently selected from the group consisting of a saturated or unsaturated, straight or branched alkyl group containing 1 to 4 carbon atoms, or an aromatic group or —$CO_2R^{13}$ in which $R^{13}$ is a saturated alkyl group containing 1 to 4 carbon atoms;

$R^{14}$, $R^{15}$, $R^{16}$ are each independently selected from the group consisting of H or $CH_3$;

$R^5$, $R^6$ and $R^7$ are each independently selected from the group consisting of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$ is different from H and $CH_3$;

or a pharmaceutically acceptable salt or food quality acceptable salt thereof.

2. The oleic acid derivatives according to claim 1, having a molecular weight ranging from about 300 to about 600 g/mol.

3. The oleic acid derivatives according to claim 1, wherein group A consists of $A^1$ with $R^1$ and $R^2$ are independently selected from the group consisting of methyl, or a saturated or unsaturated, straight or branched alkyl group containing 4 to 6 carbon atoms.

4. The oleic acid derivatives according to claim 1, wherein group A consists of $A^1$ with $R^1$ and $R^2$ are linked together so that —$R^1$-$R^2$— is —$(CH_2)_3$— or $R^1$ and $R^2$ are a saturated straight alkyl group containing 4 carbon atoms, or a pharmaceutically acceptable salt or food quality acceptable salt thereof.

5. The oleic acid derivatives according to claim 1, wherein group A consists of $A^2$ with $R^3$ is

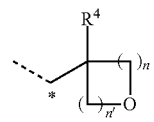

wherein
$R^4$ is $CH_3$, n=1, n'=1;
or a pharmaceutically acceptable salt or food quality acceptable salt thereof.

6. The oleic acid derivatives according to claim 1, wherein group A consists of $A^2$ with $R^3$ is

or a pharmaceutically acceptable salt or food quality acceptable salt thereof.

7. The oleic acid derivatives according to claim 1, wherein group A consists of $A^3$ with $R^5$ is H, $R^6$ is —$CO_2CH_3$ and $R^7$ is H or $R^5$ is —$CO_2CH_3$, $R^6$ is H and $R^7$ is H, or a pharmaceutically acceptable salt or food quality acceptable salt thereof.

8. A medicament comprising at least an oleic acid derivative of Formula (Z)-(I) or (E)-(I):

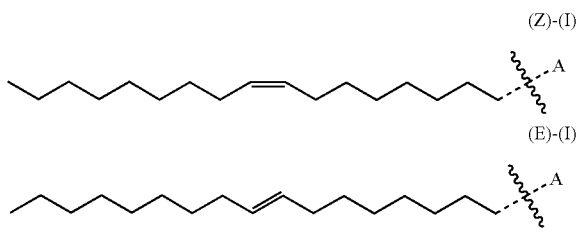

wherein group A is selected from $A^1$ to $A^3$ below:

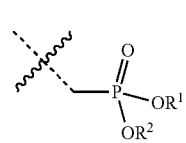

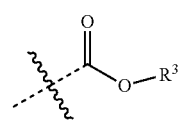

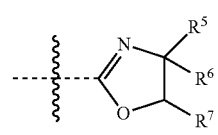

wherein
$R^1$ and $R^2$ are each independently selected from the group consisting of H or a saturated or unsaturated, straight or branched alkyl group containing 1 to 8 carbon atoms, or $R^1$ and $R^2$ are linked together to form a divalent radical of formula —$R^1$-$R^2$— wherein —$R^1$-$R^2$— is —$CH_2$—$CH_2$— or —$(CH_2)_3$—; with the proviso that:

when $R^1$ or $R^2$=H, respectively $R^2$ or $R^1$ is different from H and from a straight alkyl group containing 2 or 8 carbon atoms and when $R^1$ or $R^2$=—$CH_2CH_3$ or —$CH(CH_3)_2$ or —$(CH_2)_3CH_3$, $R^1$ and $R^2$ are not identical, $R^3$ is independently selected from the group consisting of:

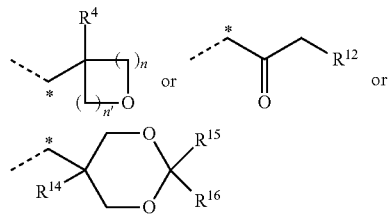

wherein $R^4$ is independently selected from the group consisting of a saturated or unsaturated, straight or branched alkyl group containing 1 to 4 carbon atoms, n is an integer selected from 1 to 4, and n' is an integer that is equal to 0 or 1; "*" is the carbon atom which is attached to the oxygen atom of the $A^2$ group;

$R^{12}$ is independently selected from the group consisting of an alkyl group containing 1 to 4 carbon atoms, or an aromatic group or —$CO_2R^{13}$ in which $R^{13}$ is a saturated alkyl group containing 1 to 4 carbon atoms, $R^{14}$, $R^{15}$, $R^{16}$ are each independently selected from the group consisting of H or $CH_3$; or $R^{14}$=H or $CH_3$ and $R^{15}$=$R^{16}$=H;

$R^5$, $R^6$ and $R^7$ are each independently selected from the group consisting of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$ is different from H and $CH_3$;

or a pharmaceutically acceptable salt or food quality acceptable salt thereof.

9. A pharmaceutical composition or food composition comprising, respectively,
at least one pharmaceutically acceptable carrier and at least one oleic acid derivative as defined in claim 8 wherein group A is selected from $A^1$ and $A^2$; or
at least one food ingredient and/or at least one food additive and at least one oleic acid derivative as defined in claim 8, wherein group A is selected from $A^1$ and $A^2$.

10. A method for treatment of a disorder modulated by the GPR120 receptor and/or the CD36 receptor, comprising:
administering to a subject in need thereof a therapeutically effective amount of an oleic acid derivative of Formula (Z)-(I) or (E)-(I)

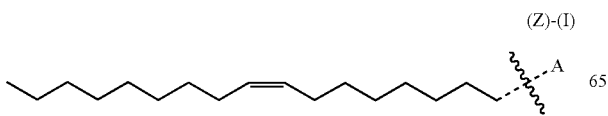

(Z)-(I)

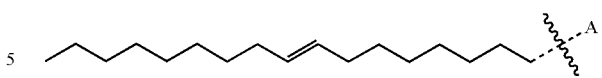

(E)-(I)

wherein said group A is selected from $A^1$ to $A^3$ below:

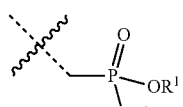

$A^1$

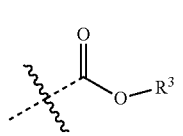

$A^2$

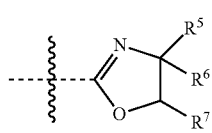

$A^3$ wherein
$R^1$ and $R^2$ are each independently selected from the group consisting of H or a saturated or unsaturated, straight or branched alkyl group containing 1 to 8 carbon atoms, or $R^1$ and $R^2$ are linked together to form a divalent radical of formula —$R^1$-$R^2$—, wherein —$R^1$-$R^2$— is —$CH_2$—$CH_2$— or —$(CH_2)_3$—;

with the proviso that:
when $R^1$ or $R^2$=H, respectively $R^2$ or $R^1$ is different from H and from a straight alkyl group containing 2 or 8 carbon atoms, and
when $R^1$ or $R^2$=—$CH_2CH_3$ or —$CH(CH_3)_2$ or —$(CH_2)_3CH_3$, $R^1$ and $R^2$ are not identical;

$R^3$ is independently selected from the group consisting of

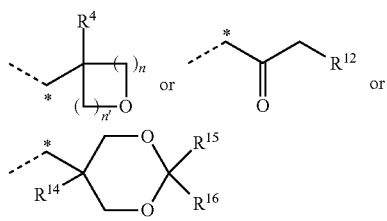

wherein $R^4$ is independently selected from the group consisting of a saturated or unsaturated, straight or branched alkyl group containing 1 to 4 carbon atoms, n is an integer selected from 1 to 4, and n' is an integer that is equal to 0 or 1; "*" is the carbon atom which is attached to the oxygen atom of the $A^2$ group;

$R^{12}$ is independently selected from the group consisting of a saturated or unsaturated, straight or branched alkyl group containing 1 to 4 carbon atoms, or an aromatic group or —$CO_2R^{13}$ in which $R^{13}$ is a saturated alkyl group containing 1 to 4 carbon atoms, $R^{14}$, $R^{15}$, $R^{16}$ are each independently selected from the group consisting of H or $CH_3$;

$R^5$, $R^6$ and $R^7$ are each independently selected from the group consisting of H or a saturated or unsaturated, straight or branched alkyl group containing 1 to 4 carbon atoms, or —$CO_2R^8$ in which $R^8$ is a saturated or unsaturated, straight or branched alkyl group containing 1 to 4 carbon atoms, with the proviso that when $R^7$ is H or $CH_3$, at least one of $R^5$ and $R^6$ is different from H and $CH_3$;

or administering to a subject in need thereof a therapeutically effective amount of the pharmaceutical composition or food composition according to claim 9.

11. An appetite suppressant comprising the oleic acid derivative according to claim 1.

12. A food supplement or dietary supplement for animal or human food, or ready-cooked dish, or animal feedstuff, comprising the food composition according to claim 9.

13. A method of enhancing taste, modulating taste, suppressing appetite, or improving the physical appearance of individuals, comprising applying an effective amount of the oleic acid derivative according to claim 1 to a food or an individual.

14. The oleic acid derivative of claim 1,
wherein group A consists of $A^2$ with
$R^4$ is $CH_3$; or
$R^{14}$=$R^{15}$=$R^{16}$=$CH_3$ or
$R^{14}$=H or $CH_3$ and $R^{15}$=$R^{16}$=H; or
wherein group A consists of $A^3$ with $R^5$ and $R^6$ are different from H or $CH_3$.

15. The oleic acid derivatives according to claim 1, having a molecular weight ranging from 330 to 460 g/mol.

16. The oleic acid derivatives according to claim 1, wherein group A consists of $A^1$.

17. The oleic acid derivatives according to claim 1, wherein group A consists of $A^1$ with $R^1$ and $R^2$ are each independently selected from the group consisting of methyl, or a saturated or unsaturated, straight or branched alkyl group containing 4 to 6 carbon atoms with the proviso that when $R^1$ or $R^2$=—$(CH_2)_3CH_3$, respectively $R^2$ or $R^1 \neq$ —$(CH_2)_3CH_3$.

18. A medicament according to claim 8, wherein in the group A of the at least an oleic acid derivative of Formula (Z)-(I) or (E)-(I):
wherein group A consists of $A^2$
with $R^{14}$=$R^{15}$=$R^{16}$=$CH_3$.

19. The method of claim 10, wherein the disorder modulated by the GPR120 receptor and/or the CD36 receptor is selected from the group consisting of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, delayed wound healing, atherosclerosis and its sequelae, abnormal heart function, congestive heart failure, myocardial ischemia, stroke, Metabolic Syndrome, hypertension, obesity, body weight disorder, fatty liver disease, dyslipidemia, hyperlipidemia, hypertriglyceridemia, hypercholesterolemia, low high-density lipoprotein (HDL), high low-density lipoprotein (LDL), lipid disorders and liver diseases.

* * * * *